(12) United States Patent
Berlowitz et al.

(10) Patent No.: US 10,093,997 B2
(45) Date of Patent: *Oct. 9, 2018

(54) INTEGRATION OF MOLTEN CARBONATE FUEL CELLS IN IRON AND STEEL PROCESSING

(71) Applicant: ExxonMobil Research and Engineering Company, Annandale, NJ (US)

(72) Inventors: Paul J. Berlowitz, Glen Gardner, NJ (US); Timothy Andrew Barckholtz, Whitehouse Station, NJ (US); Anita S. Lee, Jersey City, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 299 days.

This patent is subject to a terminal disclaimer.

(21) Appl. No.: 14/987,108

(22) Filed: Jan. 4, 2016

(65) Prior Publication Data

US 2017/0191139 A1 Jul. 6, 2017

Related U.S. Application Data

(63) Continuation of application No. 14/207,726, filed on Mar. 13, 2014, now Pat. No. 9,263,755.

(Continued)

(51) Int. Cl.
*C22B 15/00* (2006.01)
*H01M 8/00* (2016.01)
(Continued)

(52) U.S. Cl.
CPC ......... *C21B 15/00* (2013.01); *H01M 8/04014* (2013.01); *H01M 8/04761* (2013.01);
(Continued)

(58) Field of Classification Search
CPC ....... C22B 15/00; H01M 8/06; H01M 8/0693; H01M 2008/147
See application file for complete search history.

(56) References Cited

U.S. PATENT DOCUMENTS 3,615,839 A 10/1971 Thompson et al.
3,970,474 A 7/1976 Anbar et al.
(Continued)

FOREIGN PATENT DOCUMENTS

CA 2120858 A1 10/1994
CA 23250702 A1 4/2002
(Continued)

OTHER PUBLICATIONS

Avidan, "Gasoline and Distillate Fuels from Methanol", Studies in Surface Science and Catalysis, 1988, vol. 36, pp. 307-323, Methane Conversion, Elsevier Science Publishers B.V., Amsterdam.

(Continued)

*Primary Examiner* — George Wyszomierski
*Assistant Examiner* — Tima M McGuthry-Banks
(74) *Attorney, Agent, or Firm* — Liza Negron

(57) ABSTRACT

In various aspects, systems and methods are provided for operating molten carbonate fuel cells with processes for iron and/or steel production. The systems and methods can provide process improvements such as increased efficiency, reduction of carbon emissions per ton of product produced, or simplified capture of the carbon emissions as an integrated part of the system. The number of separate processes and the complexity of the overall production system can be reduced while providing flexibility in fuel feed stock and the various chemical, heat, and electrical outputs needed to power the processes.

19 Claims, 5 Drawing Sheets

Related U.S. Application Data

(60) Provisional application No. 61/788,628, filed on Mar. 15, 2013, provisional application No. 61/787,587, filed on Mar. 15, 2013, provisional application No. 61/787,697, filed on Mar. 15, 2013, provisional application No. 61/787,879, filed on Mar. 15, 2013, provisional application No. 61/884,376, filed on Sep. 30, 2013, provisional application No. 61/884,545, filed on Sep. 30, 2013, provisional application No. 61/884,565, filed on Sep. 30, 2013, provisional application No. 61/884,586, filed on Sep. 30, 2013, provisional application No. 61/884,605, filed on Sep. 30, 2013, provisional application No. 61/884,635, filed on Sep. 30, 2013, provisional application No. 61/889,757, filed on Oct. 11, 2013.

(51) Int. Cl.
| | |
|---|---|
| *C21B 15/00* | (2006.01) |
| *H01M 8/14* | (2006.01) |
| *H01M 8/04014* | (2016.01) |
| *H01M 8/04746* | (2016.01) |
| *H01M 8/04828* | (2016.01) |
| *H01M 8/06* | (2016.01) |

(52) U.S. Cl.
CPC ......... *H01M 8/04843* (2013.01); *H01M 8/06* (2013.01); *H01M 8/0693* (2013.01); *H01M 8/145* (2013.01); *H01M 2008/147* (2013.01); *H01M 2250/10* (2013.01)

(56) References Cited

U.S. PATENT DOCUMENTS

| | | |
|---|---|---|
| 4,041,210 A | 8/1977 | Van Dine |
| 4,160,663 A | 7/1979 | Hseih |
| 4,772,634 A | 9/1988 | Farooque |
| 4,810,595 A | 3/1989 | Kahara et al. |
| 4,917,971 A | 4/1990 | Farooque |
| 4,921,765 A | 5/1990 | Geisbrecht et al. |
| 4,995,807 A | 2/1991 | Rampley et al. |
| 5,039,579 A | 8/1991 | Kinoshita |
| 5,071,719 A | 12/1991 | Rostrup-Nielsen et al. |
| 5,079,103 A | 1/1992 | Schramm |
| 5,082,752 A | 1/1992 | Koga et al. |
| 5,084,362 A | 1/1992 | Farooque |
| 5,134,043 A | 7/1992 | Nakazawa |
| 5,169,717 A | 12/1992 | Topsoe |
| 5,198,311 A | 3/1993 | Nakazawa et al. |
| 5,208,113 A | 5/1993 | Kinoshita |
| 5,232,793 A | 8/1993 | Miyauchi et al. |
| 5,413,878 A | 5/1995 | Williams et al. |
| 5,417,051 A | 5/1995 | Ankersmit et al. |
| 5,380,600 A | 6/1995 | Hansen et al. |
| 5,422,195 A | 6/1995 | Bernard |
| 5,470,670 A | 11/1995 | Yasumoto et al. |
| 5,541,014 A | 7/1996 | Micheli et al. |
| 5,554,453 A | 9/1996 | Steinfeld et al. |
| 5,616,430 A | 4/1997 | Aoyama |
| 5,736,026 A | 4/1998 | Patel et al. |
| 5,833,734 A | 11/1998 | Cip et al. |
| 6,090,312 A | 7/2000 | Ziaka et al. |
| 6,126,718 A | 10/2000 | Sawa et al. |
| 6,162,556 A | 12/2000 | Vollmar et al. |
| 6,267,799 B1 | 7/2001 | Innes et al. |
| 6,322,916 B1 | 11/2001 | Hemmes et al. |
| 6,365,290 B1 | 4/2002 | Ghezel-Ayagh et al. |
| 6,383,251 B1 | 5/2002 | Sherwood |
| 6,524,356 B2 | 2/2003 | Fournier et al. |
| 6,648,942 B2 | 11/2003 | Hoffman et al. |
| 6,896,988 B2 | 5/2005 | Wang et al. |
| 7,311,986 B2 | 12/2007 | Hsu |
| 7,396,603 B2 | 7/2008 | Farooque et al. |
| 7,563,527 B2 | 7/2009 | Tanaka et al. |
| 7,862,938 B2 | 1/2011 | Ghezel-Ayagh |
| 7,914,765 B2 | 3/2011 | McLean et al. |
| 8,047,007 B2 | 11/2011 | Zubrin et al. |
| 8,080,344 B2 | 12/2011 | Skok et al. |
| 8,142,943 B2 | 3/2012 | McElroy et al. |
| 8,349,504 B1 | 1/2013 | Radovich |
| 8,562,903 B2 | 10/2013 | Hayton et al. |
| 9,263,755 B2 * | 2/2016 | Berlowitz ................. C01B 3/34 |
| 2002/0142208 A1 | 10/2002 | Keefer et al. |
| 2003/0008183 A1 | 1/2003 | Hsu |
| 2003/0143448 A1 | 7/2003 | Keefer |
| 2004/0038089 A1 | 2/2004 | Hoffman et al. |
| 2004/0202914 A1 | 10/2004 | Sridhar et al. |
| 2005/0079395 A1 | 4/2005 | Varatarajan et al. |
| 2005/0106429 A1 | 5/2005 | Keefer |
| 2005/0112425 A1 | 5/2005 | Hsu |
| 2005/0123810 A1 | 6/2005 | Balan |
| 2005/0164051 A1 | 7/2005 | Venkataraman et al. |
| 2005/0181247 A1 | 8/2005 | Foger et al. |
| 2005/0271914 A1 | 12/2005 | Farooque et al. |
| 2006/0127718 A1 | 6/2006 | Kurashima et al. |
| 2006/0159967 A1 | 7/2006 | Huijsmans et al. |
| 2006/0251940 A1 | 11/2006 | Bamdjaier et al. |
| 2007/0017367 A1 | 1/2007 | McElroy et al. |
| 2007/0072027 A1 | 3/2007 | Sridhar et al. |
| 2007/0099038 A1 | 5/2007 | Galloway |
| 2007/0184310 A1 | 8/2007 | Kim et al. |
| 2007/0224467 A1 | 9/2007 | Nervi et al. |
| 2007/0287046 A1 | 12/2007 | Koda et al. |
| 2008/0057361 A1 | 3/2008 | Moon et al. |
| 2008/0160358 A1 | 7/2008 | Parodi et al. |
| 2009/0042070 A1 | 2/2009 | Brown, Jr. et al. |
| 2009/0169452 A1 | 7/2009 | Constantz et al. |
| 2009/0208784 A1 | 8/2009 | Perry et al. |
| 2009/0317667 A2 | 12/2009 | Nervi et al. |
| 2009/0317669 A1 | 12/2009 | Hildebrandt et al. |
| 2010/0015486 A1 | 1/2010 | Yoshiba |
| 2010/0148410 A1 | 6/2010 | Bleifuss et al. |
| 2010/0239924 A1 | 9/2010 | McElroy et al. |
| 2011/0104577 A1 | 5/2011 | Cui et al. |
| 2011/0111315 A1 | 5/2011 | Cui et al. |
| 2011/0117460 A1 | 5/2011 | Shin |
| 2011/0154951 A1 | 6/2011 | Hiraoka |
| 2011/0167821 A1 | 7/2011 | Baker et al. |
| 2011/0171544 A1 | 7/2011 | Burmeister et al. |
| 2011/0223500 A1 | 9/2011 | Uematsu et al. |
| 2011/0223501 A1 | 9/2011 | Uematsu et al. |
| 2012/0028145 A1 | 2/2012 | Baden et al. |
| 2012/0171588 A1 | 7/2012 | Fan et al. |
| 2012/0214076 A1 | 8/2012 | Hakala |
| 2012/0251898 A1 | 10/2012 | Lehar et al. |
| 2012/0325053 A1 | 12/2012 | Grossi |
| 2013/0014484 A1 | 1/2013 | Caprile et al. |
| 2013/0081516 A1 | 4/2013 | Simmons |
| 2013/0177824 A1 | 7/2013 | Cui et al. |
| 2013/0209904 A1 | 8/2013 | Liu et al. |

FOREIGN PATENT DOCUMENTS

| | | |
|---|---|---|
| CN | 101098022 A | 1/2008 |
| CN | 201902241 U | 7/2011 |
| CN | 2694153 A1 | 9/2011 |
| DE | 4005468 A1 | 8/1991 |
| DE | 19515669 A1 | 10/1996 |
| DE | 19545186 A1 | 6/1997 |
| DE | 19941724 A1 | 8/2000 |
| DE | 10016847 A1 | 10/2001 |
| EP | 0170277 A2 | 5/1986 |
| EP | 0473153 A2 | 4/1992 |
| EP | 1926171 A1 | 5/2008 |
| JP | 56069775 A | 6/1981 |
| JP | H05163180 A | 6/1993 |
| JP | 08096824 A | 4/1996 |
| JP | 10172595 A | 6/1999 |
| JP | 11191427 A | 7/1999 |
| JP | 11312527 A | 11/1999 |
| JP | 2002319248 A | 10/2002 |
| JP | 2004014124 A | 1/2004 |

(56) References Cited

FOREIGN PATENT DOCUMENTS

| JP | 2004079495 A | 3/2004 |
|---|---|---|
| JP | 2004186074 A | 7/2004 |
| JP | 2006073316 A | 3/2006 |
| JP | 2007287580 A | 11/2007 |
| JP | 2008192425 A | 8/2008 |
| JP | 2008287940 A | 11/2008 |
| JP | 2009043487 A | 2/2009 |
| JP | 2013045535 A1 | 3/2013 |
| KR | 100651270 B1 | 11/2006 |
| KR | 100827954 B1 | 5/2008 |
| KR | 20090067426 A | 6/2009 |
| KR | 20090124824 A | 12/2009 |
| KR | 20110029963 A | 3/2011 |
| KR | 20110032443 A | 3/2011 |
| KR | 101032974 B1 | 5/2011 |
| KR | 20110077775 A | 7/2011 |
| KR | 20120050319 A | 5/2012 |
| NL | 1008883 C2 | 10/1999 |
| WO | 9733828 A1 | 9/1997 |
| WO | 02070402 A2 | 9/2002 |
| WO | 2002103833 A1 | 12/2002 |
| WO | 2003063276 A2 | 7/2003 |
| WO | 2004013924 A2 | 2/2004 |
| WO | 2005001977 A1 | 1/2005 |
| WO | 2008036169 A2 | 3/2008 |
| WO | 02069430 A2 | 9/2009 |
| WO | 2010044113 A1 | 4/2010 |
| WO | 2010067223 A1 | 6/2010 |
| WO | 2010125443 A1 | 11/2010 |
| WO | 2010147885 A1 | 12/2010 |
| WO | 2010147886 A1 | 12/2010 |
| WO | 2011077224 A1 | 6/2011 |
| WO | 2012091096 A1 | 7/2012 |
| WO | 2012176176 A1 | 12/2012 |
| WO | 2012176177 A1 | 12/2012 |

OTHER PUBLICATIONS

Keil, "Methanol-to-hydrocarbons: process technology" Microporous and Mesoporous Materials, Jun. 1999, vol. 29 (1-2), pp. 49-66, Elsevier.

Campanari, "Carbon Dioxide separation from high temperature fuel cell power plants", Journal of Power Sources, 2002, vol. 112, pp. 273-289, Science Direct, Elsevier.

Amorelli et al., "An experimental investigation into the use of molten carbonate fuel cells to capture CO2 from gas turbine exhaust gases", Energy, 2004, vol. 29, pp. 1279-1284, Science Direct, Elsevier.

Naqvi, "Dimethyl Ether as Fuel", SRI Consulting Report, Report No. 245A, Sep. 2005, Process Economics Program, Menlo Park, CA.

Greenhouse Gas Technology Center, "Test and Quality Assurance Plan: FuelCell Energy, Inc.—DFC 300A Molten Carbonate Fuel Cell Combined Heat and Power System" SRI/USEPA, Mar. 2007, pp. 1-42, Southern Research Institute, Morrisville, NC.

Abu-Zahra et al., "CO2 capture from power plants Part I: A parametric study of the technical performance based on monoethanolamine", International Journal of Greenhouse Gas Control, 2007, vol. 1, pp. 37-46, ScienceDirect, Elsevier.

"Molten Carbonate Fuel Cell Technology", Fossil Energy Office of Communications, Jan. 11, 2011, U.S. Department of Energy.

Campanari et al., "Application of MCFCs for active CO2 capture within natural gas combine cycles" Energy Procedia, 2011, vol. 4, pp. 1235-1242, Science Direct, Elsevier.

Caprile, "Carbon capture: Energy wasting technologies or the MCFCs challenge?", International Journal of Hydrogen Energy, 2011, vol. 36, pp. 10269-10277, Science Direct, Elsevier.

Chiesa et al., "CO2 cryagenic separation from combined cycles integrated with molten carbonate fuel cells", International Journal of Hydrogen Energy, 2011, vol. 36, pp. 10355-10365, Science Direct, Elsevier.

Wesoff, "Will FuelCell Energy Be the First Profitable Company in the Industry?", Greentech Media, Dec. 15, 2011.

Manzolini et al., "CO2 Separation from Combined Cycles Using Molten Carbonate Fuel Cells," Journal of Fuel Cell Science and Technology, Feb. 2012, pp. 011018-1 to 011018-8, vol. 9, iss. 1, American Society of Mechanical Engineers.

Zhou et al., "Decrease of energy demand for bioethanol-based polygeneration system through case study," Applied Energy, Mar. 6, 2012, vol. 95, pp. 305-311, Elsevier.

Ghezel-Ayagh, "Electrochemical Membrane for CO2 Capture and Power Generation (No. DE-FE0007634)", presentation given at the 2012 NETL CO2 Capture Technology Meeting, Jul. 9, 2012, Pittsburgh, PA.

Desideri, U., et al., "MCFC-based CO2 capture system for small scale CHP plants," International Journal of Hydrogen Energy, Dec. 2012, pp. 19295-19303, vol. 37, iss. 24, SciVerse Science Direct, Elsevier.

Ghezel-Ayagh, "High Efficiency Direct FuelCell/Turbine® Power Plant", Project Fact Sheet for unit installed at the Billings Clinic in Billings, Montana, U.S. Department of Energy.

Office Action from related U.S. Appl. No. 14/315,419 dated Aug. 1, 2014.

Office Action from related U.S. Appl. No. 14/315,419 dated Jan. 27, 2015.

Office Action from related U.S. Appl. No. 14/315,439 dated Dec. 29, 2014.

Office Action from related U.S. Appl. No. 14/315,527 dated Jan. 9, 2015.

Office Action from related U.S. Appl. No. 14/315,479 dated Nov. 7, 2014.

International Search Report with Written Opinion from PCT/US2014/025188 dated Jan. 21, 2015.

International Search Report with Written Opinion from PCT/US2014/025219 dated Jan. 21, 2015.

Cavallaro et al., "Syngas and electricity production by an integrated autothermal reforming/molten carbonate fuel cell system", Journal of Power Sources, Dec. 1, 1988 pp. 190-196, vol. 76, No. 2, Elsevier.

Appleby et al., "Current Technology of PAFC, MCFC and SOFC Systems: Status of Present Fuel Cell Power Plants", Electrochemical Hydrogen Technologies, Electrochemical Production and Combustion of Hydrogen, Jan. 1, 1990, pp. 425-495, Elsevier.

Appleby, "Fuel Cells and Hydrogen Fuel", International Journal of Hydrogen Energy, Feb. 1, 1994, pp. 175-180 vol. 19, No. 2, International Association for Hydrogen Energy, Pergamon Press Ltd., Great Britain.

Chiesa et al., "A Comparative Analysis of IGCCs with CO2 Sequestration", In: Proceedings of 4th International Conference on Greenhouse Gas Control Technologies, Interlaken, Switzerland Aug. 30, 1998-Sep. 2, 1998, pp. 107-112.

Amorelli et al., "An experimental investigation into the use of molten carbonate fuel cells to capture CO2 from gas turbine exhaust gases", 2nd annual conference on Carbon Seqquestration, May 5, 2003 to May 8, 2003, Hilton Alexandria Mark Center, Alexandria, VA.

Sugiura et al., "The carbon dioxide concentrator by using MCFC", Journal of Power Sources, May 25, 2003, pp. 218-227, vol. 118, No. 1-2, ScienceDirect, Elsevier.

Steynberg et al., eds., "Gas loop for POX reformers", Studies in Surface Science and Catalysis: Fischer Tropsch Technology, Jul. 28, 2004, vol. 152, p. 432, fig. 8, Elsevier B.V.

Verda et al., "Thermodynamic and economic optimization of a MCFC-based hybrid system for the combined production of electricity and hydrogen". International Journal of Hydrogen Energy, Jan. 1, 2010, vol. 35, No. 2, pp. 794-806, ScienceDirect, Elsevier.

Campanari et al., "CO2 capture from combined cycles integrated with Molten Carbonate Fuel Cells", International Journal of Greenhouse Gas Control, May 1, 2010, pp. 441-451, vol. 4, No. 3, Greenhouse Gas Control, ScienceDirect, Elsevier.

Kim et al., "Numerical studies of a separator for stack temperature control in a molten carbonate fuel cell", International Journal of Hydrogen Energy, Apr. 7, 2011, vol. 36, No. 14, pp. 8499-8507, ScienceDirect, Elsevier.

(56) References Cited

OTHER PUBLICATIONS

Pilatowski et al., "Thermodynamics of Fuel Cells", Cogeneration Fuel Cell-Sorption Air Conditioning Systems, Jun. 2, 2011, pp. 25-36, Springer.
Lowe et al., "Technology Assessment of Hydrogen Firing of Process Heaters", Energy Procedia, Jul. 1, 2011, pp. 1058-1065, vol. 4, ScienceDirect, Elsevier.
Appl, "Ammonia, 3. Production Plants", Ullmann's Encyclopedia of Industrial Chemistry, Oct. 15, 2011, vol. 3, Wiley-Verlag GmbH & Co., Weinheim.
Anonymous, "Lower and Higher Heating Values of Fuels", Hydrogen Data Resource Center: Hydrogen Calculator, Jan. 1, 2012, U.S. Dept. of Energy.
Giddey et al., "A comprehensive review of direct carbon fuel cell technology", Progress in Energy Combustion Science, Jan. 28, 2012, pp. 360-399, vol. 38, No. 3, Science Direct, Elsevier.
Anonymous, "Heat of Combustion", Wikipedia, the free Encyclopedia, Jun. 6, 2014.
International Search Report with Written Opinion from PCT/US2014/025173 dated Jun. 13, 2014.
International Search Report with Written Opinion from PCT/US2014/025214 dated Jul. 4, 2014.
International Search Report with Written Opinion from PCT/US2014/025228 dated Jul. 4, 2014.
International Search Report with Written Opinion from PCT/US2014/025237 dated Jul. 4, 2014.
International Search Report with Written Opinion from PCT/US2014/025181 dated Jul. 7, 2014.
International Search Report with Written Opinion from PCT/US2014/025186 dated Jul. 7, 2014.
International Search Report with Written Opinion from PCT/US2014/025189 dated Jul. 7, 2014.
International Search Report with Written Opinion from PCT/US2014/025240 dated Jul. 8, 2014.
International Search Report with Written Opinion from PCT/US2014/025216 dated Jul. 15, 2014.
International Search Report with Written Opinion from PCT/US2014/025223 dated Jul. 15, 2014.
International Search Report with Written Opinion from PCT/US2014/025192 dated Jul. 22, 2014.
International Search Report with Written Opinion from PCT/US2014/025208 dated Jul. 22, 2014.
International Search Report with Written Opinion from PCT/US2014/025195 dated Jul. 24, 2014.
International Search Report with Written Opinion from PCT/US2014/025180 dated Jul. 28, 2014.
International Search Report with Written Opinion from PCT/US2014/025175 dated Jul. 28, 2014.
International Search Report with Written Opinion from PCT/US2014/025185 dated Jul. 28, 2014.
International Search Report with Written Opinion from PCT/US2014/025212 dated Jul. 28, 2014.
International Search Report with Written Opinion from PCT/US2014/025179 dated Aug. 5, 2014.
International Search Report with Written Opinion from PCT/US2014/025229 dated Aug. 5, 2014.
Partial International Search Report from PCT/US2014/025188 dated Aug. 29, 2014.
Partial International Search Report from PCT/US2014/025219 dated Aug. 29, 2014.
International Search Report with Written Opinion from PCT/US2014/025203 dated Sep. 1, 2014.

* cited by examiner

|        | 401    | 402   | 403    | 404    | 405    | 406    | 407    | 408    | 409    |
|--------|--------|-------|--------|--------|--------|--------|--------|--------|--------|
| T [C]  |        | 30    | 532    | 616    | 1200   | 700    | 631    | 523    | 30     |
| [kg/hr]|        |       |        |        |        |        |        |        |        |
| CH4    |        | 80510 | 23487  | 23487  | 23487  | 23432  | 23432  | 23432  | 90     |
| C2H6   |        |       |        |        |        |        |        |        |        |
| C3H8   |        |       |        |        |        |        |        |        |        |
| C4H10  |        |       |        |        |        |        |        |        |        |
| H2O    | 181310 |       | 186188 | 195021 | 236609 | 275234 | 275234 | 275234 | 301233 |
| CO2    |        | 0     | 363109 | 341590 | 240239 | 153914 | 153914 | 153914 | 8554   |
| H2     |        | 0     | 13867  | 12879  | 8236   |        |        |        |        |
| CO     |        | 0     | 38178  | 51912  | 116418 |        |        |        |        |
| N2     |        |       |        |        |        |        |        |        |        |
| O2     |        |       |        |        |        |        |        |        |        |
| Ar     |        |       |        |        |        |        |        |        |        |

|        | 410    | 411    | 412    | 413    | 414   | 415    | 416    |
|--------|--------|--------|--------|--------|-------|--------|--------|
| T      | 30     | 30     | 30     | 30     | 30    | 1210   | 536    |
| [kg/hr]|        |        |        |        |       |        |        |
|        | 23507  | 8768   | 14739  |        |       |        |        |
| CH4    |        |        |        |        | 1604  |        |        |
| C2H6   |        |        |        |        |       |        |        |
| C3H8   |        |        |        |        |       |        |        |
| C4H10  |        |        |        |        |       |        |        |
| H2O    | 8591   | 3306   | 5389   |        |       | 123183 | 123183 |
| CO2    | 414702 | 154684 | 260018 |        |       | 403899 | 403899 |
| H2     |        |        |        |        |       |        |        |
| CO     |        |        |        |        |       |        |        |
| N2     |        |        |        | 740742 |       | 740742 | 740742 |
| O2     |        |        |        | 224919 |       | 15692  | 15692  |
| Ar     |        |        |        |        |       |        |        |

FIG. 5

INTEGRATION OF MOLTEN CARBONATE FUEL CELLS IN IRON AND STEEL PROCESSING

CROSS-REFERENCE TO RELATED APPLICATIONS

This application is a Continuation of U.S. Ser. No. 14/207,726, filed Mar. 13, 2014, now allowed ("the '726 application), which claims the benefit of U.S. Ser. Nos. 61/787,587, 61/787,697, 61/787,879, and 61/788,628, all filed on Mar. 15, 2013, each of which is incorporated by reference herein in its entirety. The '726 application also claims the benefit of U.S. Ser. Nos. 61/884,376, 61/884,545, 61/884,565, 61/884,586, 61/884,605, and 61/884,635, all filed on Sep. 30, 2013, each of which is incorporated by reference herein in its entirety. The '726 application further claims the benefit of U.S. Ser. No. 61/889,757, filed on Oct. 11, 2013, which is incorporated by reference herein in its entirety.

The '726 application is related to 4 other co-pending, commonly assigned U.S. patent applications, filed on Mar. 5, 2014 as follows: Ser. Nos. 14/197,391; 14/197,430; 14/197,551; and 14/197,613. The '726 application is also related to the following 21 co-pending, commonly assigned U.S. patent applications, filed on Mar. 13, 2014: Ser. Nos. 14/207,686; 14/207,686; 14/207,688; 14/207,687; 14/207,690; 14/207,696; 14/207,698; 14/207,704; 14/207,706; 14/207,691; 14/207,693; 14/207,697; 14/207,699; 14/207,700; 14/207,705; 14/207,708; 14/207,711; 14/207,714; 14/207,710; 14/207,712; 14/207,721; and 14/207,728. Each of these co-pending U.S. applications is hereby incorporated by reference herein in its entirety.

FIELD OF THE INVENTION

In various aspects, the invention is related to use of molten carbonate fuel cells in processing and/or production of iron or steel.

BACKGROUND OF THE INVENTION

Modern methods for production of iron and steel from iron ore still have a recognizable link to early historical methods despite ongoing research to improve the process. Conventional techniques still involve heating of iron ore in a furnace in the presence of a solid carbon-containing material such as coke. Due to the nature of the process, including the substantial heat requirements for forming molten iron (and other metals), conventional processes for reducing iron oxides to form iron also result in generation of substantial quantities of carbon dioxide. This is due in part to use in typical processes of coal or other highly polluting fuels to provide the necessary heat.

Molten carbonate fuel cells utilize hydrogen and/or other fuels to generate electricity. Options for generating hydrogen for use in a molten carbonate fuel cell include reforming methane or other reformable fuels within the anode of the fuel cell, or reforming fuel in an associated reforming zone that is either internal to or external to the fuel cell. Reformable fuels can encompass hydrocarbonaceous materials that can be reacted with steam and/or oxygen at elevated temperature and/or pressure to produce a gaseous product that comprises hydrogen.

Traditionally, molten carbonate fuel cells are operated to maximize electricity production per unit of fuel input, which may be referred to as the fuel cell's electrical efficiency. This maximization can be based on the fuel cell alone or in conjunction with another power generation system. In order to achieve increased electrical production and to manage the heat generation, fuel utilization within a fuel cell is typically maintained at 70% to 75%.

U.S. Published Patent Application 2011/0111315 describes a system and process for operating fuel cell systems with substantial hydrogen content in the anode inlet stream. The technology in the '315 publication is concerned with providing enough fuel in the anode inlet so that sufficient fuel remains for the oxidation reaction as the fuel approaches the anode exit. To ensure adequate fuel, the '315 publication provides fuel with a high concentration of $H_2$. The $H_2$ not utilized in the oxidation reaction is recycled to the anode for use in the next pass. On a single pass basis, the $H_2$ utilization may range from 10% to 30%. The '315 reference does not describe significant reforming within the anode, instead relying primarily on external reforming.

U.S. Published Patent Application 2005/0123810 describes a system and method for co-production of hydrogen and electrical energy. The co-production system comprises a fuel cell and a separation unit, which is configured to receive the anode exhaust stream and separate hydrogen. A portion of the anode exhaust is also recycled to the anode inlet. The operating ranges given in the '810 publication appear to be based on a solid oxide fuel cell. Molten carbonate fuel cells are described as an alternative.

U.S. Published Patent Application 2003/0008183 describes a system and method for co-production of hydrogen and electrical power. A fuel cell is mentioned as a general type of chemical converter for converting a hydrocarbon-type fuel to hydrogen. The fuel cell system also includes an external reformer and a high temperature fuel cell. An embodiment of the fuel cell system is described that has an electrical efficiency of about 45% and a chemical production rate of about 25% resulting in a system coproduction efficiency of about 70%. The '183 publication does not appear to describe the electrical efficiency of the fuel cell in isolation from the system.

U.S. Pat. No. 5,084,362 describes a system for integrating a fuel cell with a gasification system so that coal gas can be used as a fuel source for the anode of the fuel cell. Hydrogen generated by the fuel cell is used as an input for a gasifier that is used to generate methane from a coal gas (or other coal) input. The methane from the gasifier is then used as at least part of the input fuel to the fuel cell. Thus, at least a portion of the hydrogen generated by the fuel cell is indirectly recycled to the fuel cell anode inlet in the form of the methane generated by the gasifier.

An article in the Journal of Fuel Cell Science and Technology (G. Manzolini et. al., *J. Fuel Cell Sci. and Tech.*, Vol. 9, February 2012) describes a power generation system that combines a combustion power generator with molten carbonate fuel cells. Various arrangements of fuel cells and operating parameters are described. The combustion output from the combustion generator is used in part as the input for the cathode of the fuel cell. One goal of the simulations in the Manzolini article is to use the MCFC to separate $CO_2$ from the power generator's exhaust. The simulation described in the Manzolini article establishes a maximum outlet temperature of 660° C. and notes that the inlet temperature must be sufficiently cooler to account for the temperature increase across the fuel cell. The electrical efficiency (i.e. electricity generated/fuel input) for the MCFC fuel cell in a base model case is 50%. The electrical efficiency in a test model case, which is optimized for $CO_2$ sequestration, is also 50%.

An article by Desideri et al. (*Intl. J. of Hydrogen Energy*, Vol. 37, 2012) describes a method for modeling the performance of a power generation system using a fuel cell for $CO_2$ separation. Recirculation of anode exhaust to the anode inlet and the cathode exhaust to the cathode inlet are used to improve the performance of the fuel cell. The model parameters describe an MCFC electrical efficiency of 50.3%.

U.S. Patent Application Publication 2013/0081516 describes a method for direct production of iron slabs and nuggets from ore without pelletizing or briquetting. The method involves forming a mixture of fine particles of iron ore with fine particles of a carbon source such as biomass, coke, or coal. The mixture of fine particles is passed through a linear furnace to form metallic iron. An excess of biomass, coke, or coal can be used to allow excess production of CO and $H_2$ that can be recovered as syngas from a gas phase environment in the furnace.

U.S. Pat. No. 6,524,356 describes a method for performing direct iron reduction in a shaft furnace using reformed methane as a source of synthesis gas. The method further describes introducing additional natural gas into the shaft furnace as a source of carbon for incorporation into the iron.

SUMMARY OF THE INVENTION

In an aspect, a method is provided for producing iron or steel. The method includes introducing a fuel stream comprising a reformable fuel into the anode of a molten carbonate fuel cell, an internal reforming element associated with the anode, or a combination thereof; introducing a cathode inlet stream comprising $CO_2$ and $O_2$ into the cathode of the fuel cell; generating electricity within the molten carbonate fuel cell; withdrawing, from an anode exhaust, a gas stream comprising CO, the anode exhaust having a pressure of about 500 kPag or less; and introducing the gas stream withdrawn from the anode exhaust into a process for production of iron, steel, or a combination thereof.

BRIEF DESCRIPTION OF THE FIGURES

FIG. 5 shows process flows for an example of integration of molten carbonate fuel cells with a process for producing iron or steel.

DETAILED DESCRIPTION OF THE EMBODIMENTS

Overview

Figure 1:
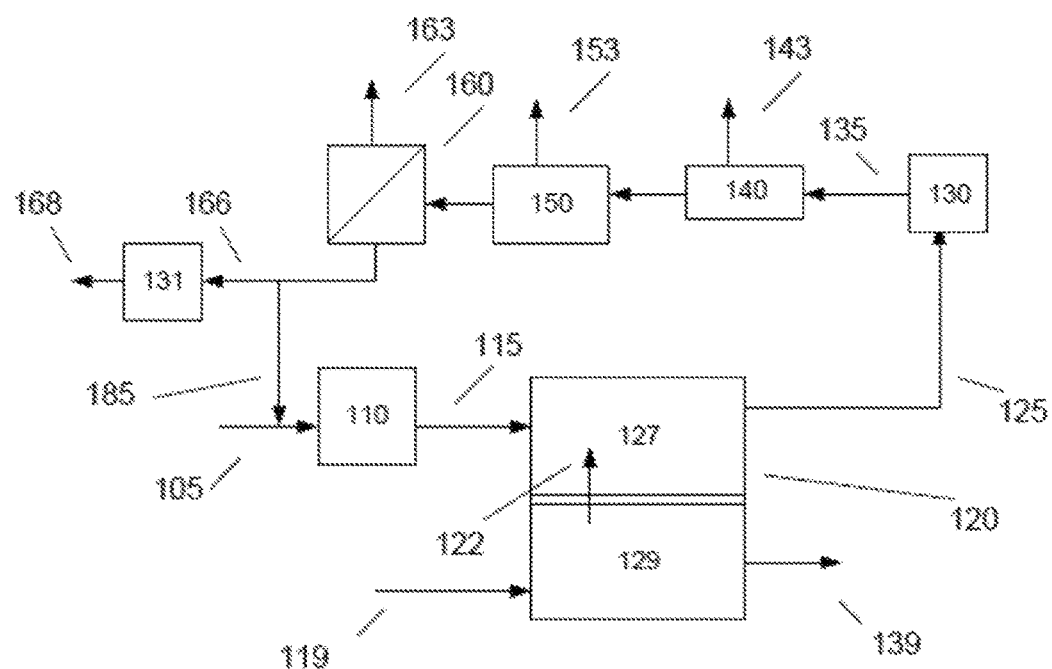
FIG. 1 schematically shows an example of a configuration for molten carbonate fuel cells and associated reforming and separation stages.

In various aspects, the operation of molten carbonate fuel cells can be integrated with a variety of chemical and/or materials production processes, including but not limited to processes for production of iron and/or steel. The production processes can correspond to production of an output from the molten carbonate fuel cells, or the production process can consume and/or provide one or more fuel cell streams. Integration with Iron or Steel Manufacture In various aspects, processes are provided that integrate the production of iron and/or steel with the use of an MCFC system. Iron can be produced from the reduction of iron oxides present in iron ore. The reaction can require high temperatures, such as up to 2000° C., more typically from about 800° C. to about 1600° C., and a reductant that can remove tightly bound oxygen from iron oxide that can be used in the blast furnace to produce iron metal. The most widely used method involves the processing of coal to produce coke and subsequently to produce a blast furnace gas comprising CO as the primary chemical reductant. The process can typically also require a substantial amount of heat, and frequently significant amounts of electricity used both in the basic process itself, and in subsequent steelmaking processing. The electrical requirements may include typical plant needs for operating pumps, valves and other machinery as well as large, direct electrical inputs such as for direct-reduction iron processing, electric furnace steelmaking, and similar processes. Substantial amounts of water can be needed in steelmaking beyond the water simply used for cooling, as water can be used to process coal, directly remove scale from steel, for steam generation, hydraulics and other systems.

In a conventional iron production process, the furnace gas can comprise a significant amount of CO, as well as some amounts of $H_2$, $H_2O$, $N_2$, optionally but typically sulfur (such as $H_2S$), and optionally but typically one or more other various gases derived from coal. As iron can be an effective water-gas shift catalyst, the four water-gas shift molecules (CO, $CO_2$, $H_2O$, $H_2$) can typically be at or near equilibrium in the process. CO can react with iron oxides to produce $CO_2$ and reduced iron, while incorporating some carbon into the reduced iron. This carbon can then be partially removed, for instance by controlled oxidation, to the desired level for making various grades of iron and steel products. The role of the coal and coke in a conventional iron production process can be two-fold. First, the coal or coke can provide the reductant for conversion of iron oxides to iron. Second, coal or coke can be combusted to provide heat to maintain the very high furnace temperatures. The process can typically take place at or near atmospheric pressures. In a conventional process, effluent blast furnace gas still can typically contain some amounts of combustible materials that can then be burned for additional heat.

Disadvantages of conventional processes can include the production of large quantities of $CO_2$ for every ton of iron or steel produced. In addition to the coal and coke used in a process, a flux (typically a carbonate such as $CaCO_3$ or mixture of carbonates and other materials) can be decomposed in the process releasing additional $CO_2$. To capture or reduce the amount of $CO_2$ emanating from the furnace can require separation of $CO_2$ from the various exhaust systems which can be difficult, and which can involve a number of collection, concentration and clean-up steps.

In various aspects, integrating operation of molten carbonate fuel cells with processes for iron and/or steel production can provide process improvements including but not limited to increased efficiency, reduction of carbon emissions per ton of product produced, and/or simplified capture of the carbon emissions as an integrated part of the system. The number of separate processes and the complexity of the overall production system can be reduced while providing flexibility in fuel feed stock and the various chemical, heat, and electrical outputs needed to power the processes.

In additional or alternate aspects, the combined MCFC and iron production system can allow for efficient collection of carbon with simpler systems while providing flexibility in heating. Additionally or alternatively, the combined MCFC and iron production system can incorporate direct production of electricity that can be utilized as part of the entire electrical input to the plant. As the electricity is produced on-site, transmission losses can be reduced or minimized and potential losses produced when converting AC to DC power can additionally or alternatively be avoided. Furthermore, the carbon in the fuel utilized to produce electricity can be incorporated into the same carbon capture systems used for capture of carbon dioxide from the blast furnace exhaust (or exhaust from another type of furnace used for iron or steel production). The proposed system can be designed for variable production of reductant (CO), heat, and electrical output, allowing it to be adapted to a broad range of iron and steelmaking processes and technologies using the same core components.

In an aspect, an MCFC system can be used to form an anode exhaust stream containing excess $H_2$ and/or CO (syngas). The excess syngas from the MCFC anode exhaust can be withdrawn and used to perform iron or steel production while reducing, minimizing, or eliminating the use of coke. The anode exhaust from the MCFC can be exhausted at a pressure of about 500 kPag or less, such as about 400 kPag or less, or about 250 kPag or less. For example, one can take syngas produced or withdrawn from the anode exhaust, separate at least a portion of the $H_2$ from the CO, fire the furnace with the $H_2$, perform the reduction of iron with the CO, and then consume the resulting $CO_2$ from the iron production process in the MCFC and capture it, leading to a substantial reduction in $CO_2$ emissions from the process. In such aspects, the MCFC can act as both a management system for carbon oxides (source of CO, sink of $CO_2$) and as a source of supplemental inputs to the iron or steel production process, such as by providing $H_2$ for heating, heat exchange with input and exhaust streams for efficiency, carbon capture, and/or clean process water creation. It is noted that various steel processes can additionally or alternately use electrical energy that can be provided by the MCFC system. For example, steel production can involve the use of arc furnaces, and direct reduction of iron can be done with electrical current. In various aspects, the furnaces used in an integrated system including an MCFC can be electrically heated or heated by other indirect methods that can generally allow combustion of the syngas in the furnace to be avoided.

As an example of integration of molten carbonate fuel cells in a reaction system for producing iron or steel, the reductant gas to a blast furnace can be provided by first introducing methane or other reformable fuel into an MCFC anode where the MCFC can be used to produce both electricity (such as for use by the plant) and syngas from the anode output. The MCFC system can preferably be sized such that the amount of syngas produced can be sufficient to provide all or substantially all of the CO reductant needed for the iron or steel making process. Optionally, a portion of the CO for the iron or steel making process can additionally or alternately be introduced as part of the iron ore or other iron oxide feed to the furnace. Depending on the types of processes involved, which may require larger amounts of electricity (for example, in a direct reduction steel making process) or smaller amounts of electricity, electricity may be returned to grid or drawn from the grid, to balance the energy inputs from the plant. Alternatively, the MCFC can be sized so that it can produce both all the electrical energy and reductant needed, with the MCFC being operated at a fuel utilization that balances the two main outputs to suit the plant requirements. The flexibility of the system can allow for adjusting this ratio (by adjusting fuel utilization, voltage, and/or input/output temperatures, among other variables) to adapt to changing processes or process conditions within a given plant.

Optionally but preferably, an MCFC system integrated with iron or steel production can be operated at low fuel utilization, to increase the amount of syngas available to be produced/withdrawn from the anode exhaust. While this may not be necessary, as most MCFC operations can typically produce an anode effluent comprising syngas, it can sometimes be preferable to maximize the production of anode syngas. For example, the fuel utilization can be at least about 25%, such as at least about 30%, or at least about 35%, or at least about 40%. Additionally or alternatively, the fuel utilization can be about 60% or less, such as about 55% or less, or about 50% or less, or about 45% or less, or about 40% or less. Use of a low fuel utilization value can allow for an increased content of $H_2$ and CO in the anode output. The anode output can then be used as a source of reducing gas for the blast furnace. If desired, the fuel utilization can be adjusted so that the syngas output can be in balance with the electrical requirements of the overall plant. This can potentially avoid the need for separate grid-power and can provide energy self-sufficiency to the plant with only a single fuel source feeding a single power production system; the MCFC in such a situation could provide both the electrical and chemical constituents needed for plant operations. Alternatively, the plant may utilize a separate electrical generation system such as a turbine in conjunction with an MCFC system, such that some electrical power can be produced by both systems, and so that the MCFC system can be optimized for syngas production. The size, available fuel sources, intrinsic electrical demand and other factors may result in any of these combinations being an (the most) efficient and/or economically advantageous arrangement.

In various aspects, the fuel input for an MCFC in an integrated iron or steel production system can preferentially comprise or be methane or natural gas, but can indeed be any hydrocarbonaceous material compatible with an MCFC. For hydrocarbonaceous materials that cannot be directly reformed within the MCFC (e.g. C2-C5 light gases), a pre-reformer can be employed to convert the input fuel to methane plus a syngas mixture. In such situations, preferably the anode input gas can contain a large or predominant percentage of a reformable gas and may contain amounts of syngas constituents and inerts. The anode input can preferably have impurities such as sulfur removed, which may be accomplished by conventional systems, and which can vary depending on the source and purity of the input fuel. Input fuels such as coal and/or other solid fuels can be used, if first converted to mixtures comprising reformable fuels from which impurities are removed. Inputs to the cathode can be derived primarily from iron reduction process exhaust and may contain other streams containing one or more of $CO_2$, $H_2O$, $O_2$, and inerts. Air/oxygen containing streams may be added to provide sufficient oxygen for the cathode and can typically require oxygen amounts in the overall cathode exhaust to be in excess of the total $CO_2$ amounts.

Syngas effluent from the anode outlet can be sent to a separation process where $CO_2$ and possibly some water can be removed from the stream. The separation system can be designed to remove enough $H_2O$ and $CO_2$ to produce a syngas composition that, when equilibrated in the iron reduction process conditions in the blast furnace, can have an appropriate amount of CO relative to other gas components. As opposed to conventional processes, the CO produced can be largely free from impurities such as sulfur, simplifying the need for pollutant control systems around the overall iron or steel-making plant which would normally be required when utilizing coal and/or coke. After the consumption of CO in the iron reduction process, $CO_2$ can be produced in the effluent from the process. This $CO_2$-enriched effluent stream can then be used as the input to the MCFC cathode, after appropriate heat exchange if desired. This can typically involve steam generation, which can then feed secondary electricity production from a steam turbine. For example, the effluent gas may contain combustible materials which can then be burned to produce further heat by the addition of air or oxygen. The heat produced can be used in various plant processes, but the $CO_2$ produced by the combustion can remain in the flue gas, which, when subsequently introduced into the cathode, can be concentrated/captured effectively by the MCFC system.

Separate combustion of fuel for heating the MCFC system can be reduced or minimized in any of the above systems, as sufficient waste heat for heat exchange should typically be available from the iron or steel production processes. Preferably, lower fuel utilization can be employed, as operating under such conditions can produce higher CO production per fuel cell array employed and greater carbon capture per MCFC array employed. The blast furnace off gas can additionally or alternately be heat integrated with the MCFC inlet/outlet. A portion of the blast furnace off gas can be used as at least a portion (or potentially all) of the cathode feed, while the remainder of the blast furnace off gas can be emitted to the atmosphere and/or compressed for $CO_2$ sequestration in a low $CO_2$ emissions iron or steel production scheme.

In another embodiment, the $H_2$ and CO can be separated after production by the anode, and the $H_2$ can optionally but preferably be used to provide carbon-free heating for the various plant processes, while the CO can optionally but preferably be used in the iron reduction. This can allow for fewer $CO_2$ sources within the overall plant and may simplify $CO_2$ collection for introduction as cathode feed gas.

An advantage of the MCFC system over conventional carbon capture systems, such as amine capture, can include a lack of criticality for the $CO_2$ separation system to capture a relatively high percentage (e.g. at least about 90% or at least about 95%, by volume) of the $CO_2$ from the anode. As opposed to conventional capture technologies, any carbon (as CO or $CO_2$) not captured can be converted to $CO_2$, recycled from the iron reduction process to the cathode inlet, and then (typically) mostly converted to carbonate ions to be transported across the MCFC membrane to the anode, where they can undergo the $CO_2$ separation process. The only $CO_2$ emission from the system in such a configuration can come from the cathode exhaust. The overall $CO_2$ capture efficiency of the plant can be adjusted based on the ratio of the cathode out $CO_2$ concentration relative to the cathode input $CO_2$ concentration, which can be easily varied, such as by adjusting the number of operation stages of the MCFC arrays and/or by adjusting the number of MCFC cells to increase the available fuel cell area.

Figure 4:
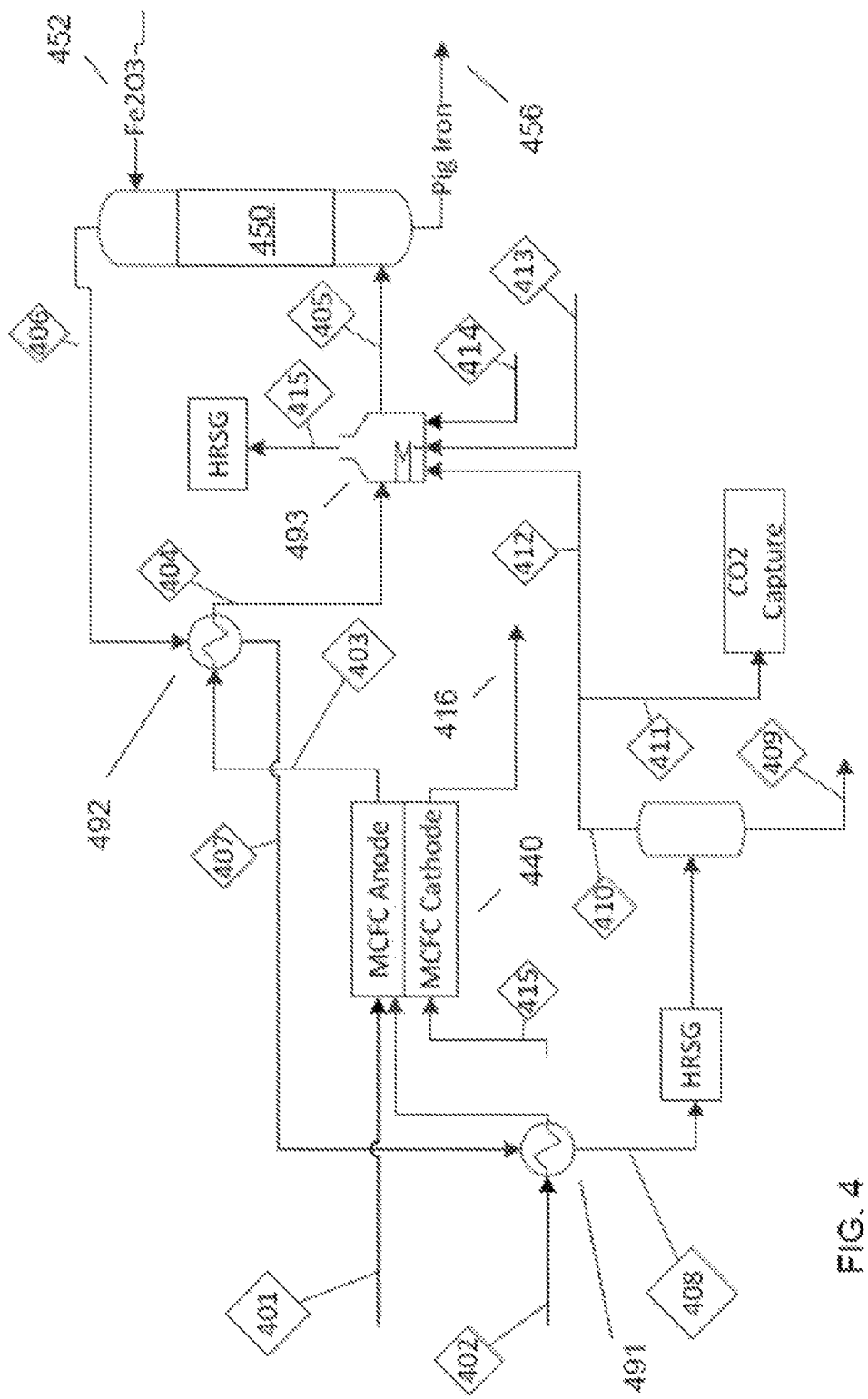
FIG. 4 schematically shows an example of integration of molten carbonate fuel cells with a process for producing iron or steel.

FIG. 4 shows an example of a configuration suitable for operating molten carbonate fuel cells (MCFCs) in conjunction with an iron reduction process. The FIG. 4 configuration can be suitable for reducing iron oxides, such as $Fe_2O_3$ and/or other iron oxides found in various types of iron ore, to pig iron (about 95% Fe). In FIG. 4, steam 401 and pre-heated methane 402 can be fed to the anode of the MCFC 440. Optionally but preferably, the methane 402 can be pre-heated via a heat exchanger 491 by recovering heat from stream 407 derived from the blast furnace off gas. The MCFC 440, such as an MCFC operating at about 30% fuel utilization, can produce reducing gases (e.g., CO and $H_2$) in the anode exhaust 403 that can be sent to the blast furnace. Anode exhaust 403 can optionally but preferably be heated, e.g., by recovering some of the heat from the blast furnace off gas 406 in heat exchanger 492. The heated anode exhaust 404 can be heated to the blast furnace inlet gas temperature (for example about 1200° C.) in pre-heater 493, resulting in an inlet gas stream 405. Conventional methods can be used for introduction 452 of solid particles of iron oxides into the top of the blast furnace 450. Optionally, the input flow 452 of particles of iron oxides can be introduced along with a flux agent, such as $CaCO_3$, that can assist with formation of a slag that can be readily separated from the iron product. The input flow 452 of particles of iron oxides can flow through the blast furnace 450 counter current to the reducing gas 405, which can enter the blast furnace 450 at a location typically more toward the bottom. Reduced Fe can leave the furnace as a bottoms flow 456, while a furnace off gas comprising $CO_2$ and $H_2O$ can leave the furnace as 406. Furnace off gas 406 can be integrated with the process to heat the anode exhaust 403 in heat exchanger 492 and/or pre-heat anode input flow 402 in heat exchanger 491. These heat recovery processes can result in a cooled furnace off gas stream 408. Optionally, further heat can be removed from furnace off gas stream 408 using a heat recovery steam generator (HRSG). Water can be condensed from the cooled off gas stream 408 in condensor 494, producing process water 409 and a gas 410 with a relatively high concentration of $CO_2$. Gas 410 can optionally also contain some methane. A fraction of gas stream 410 can be split off as a feed stream 412 to a burner and can be burned using an oxidizing source (air) 413 and a fuel (methane) 414 to produce enough $CO_2$ at an appropriate temperature for the cathode feed 415. The remainder of gas 410 can be sent 411 to a $CO_2$ separator/compression system, for instance to produce pipeline quality $CO_2$ for use and/or sequestration or alternately to be emitted to the atmosphere. Some heat from burning streams 412, 413, and 414 can additionally or alternately be used to heat stream 404. A heat recovery steam generator (HRSG) can be used to remove any additional heat in 415 before it is sent to the cathode and to generate steam for the downstream steel manufacturing processes. The MCFC can remove a convenient or desired portion of the $CO_2$, for example, at least about 50% or at least about 70% of the $CO_2$ in 415, giving a reduced $CO_2$ exhaust stream 416. Exhaust stream 416 can be emitted to the atmosphere and/or recycled back as part of cathode input stream 415.

Additional Fuel Cell Operation Strategies

As an addition, complement, and/or alternative to the fuel cell operating strategies described herein, a molten carbonate fuel cell can be operated so that the amount of reforming can be selected relative to the amount of oxidation in order to achieve a desired thermal ratio for the fuel cell. As used herein, the "thermal ratio" is defined as the heat produced by exothermic reactions in a fuel cell assembly divided by the endothermic heat demand of reforming reactions occurring within the fuel cell assembly. Expressed mathematically, the thermal ratio (TH)=$Q_{EX}/Q_{EN}$, where $Q_{EX}$ is the sum of heat produced by exothermic reactions and $Q_{EN}$ is the sum of heat consumed by the endothermic reactions occurring within the fuel cell. Note that the heat produced by the exothermic reactions corresponds to any heat due to reforming reactions, water gas shift reactions, and the electrochemical reactions in the cell. The heat generated by the electrochemical reactions can be calculated based on the ideal electrochemical potential of the fuel cell reaction across the electrolyte minus the actual output voltage of the fuel cell. For example, the ideal electrochemical potential of the reaction in a MCFC is believed to be about 1.04V based on the net reaction that occurs in the cell. During operation of the MCFC, the cell will typically have an output voltage less than 1.04 V due to various losses. For example, a common output/operating voltage can be about 0.7 V. The heat generated is equal to the electrochemical potential of the cell (i.e. ~1.04V) minus the operating voltage. For example, the heat produced by the electrochemical reactions in the cell is ~0.34 V when the output voltage of ~0.7V. Thus, in this scenario, the electrochemical reactions would produce ~0.7 V of electricity and ~0.34 V of heat energy. In such an example, the ~0.7 V of electrical energy is not included as part of $Q_{EX}$. In other words, heat energy is not electrical energy.

In various aspects, a thermal ratio can be determined for any convenient fuel cell structure, such as a fuel cell stack, an individual fuel cell within a fuel cell stack, a fuel cell stack with an integrated reforming stage, a fuel cell stack with an integrated endothermic reaction stage, or a combination thereof. The thermal ratio may also be calculated for different units within a fuel cell stack, such as an assembly of fuel cells or fuel cell stacks. For example, the thermal ratio may be calculated for a single anode within a single fuel cell, an anode section within a fuel cell stack, or an anode section within a fuel cell stack along with integrated reforming stages and/or integrated endothermic reaction stage elements in sufficiently close proximity to the anode section to be integrated from a heat integration standpoint. As used herein, "an anode section" comprises anodes within a fuel cell stack that share a common inlet or outlet manifold.

In various aspects of the invention, the operation of the fuel cells can be characterized based on a thermal ratio. Where fuel cells are operated to have a desired thermal ratio, a molten carbonate fuel cell can be operated to have a thermal ratio of about 1.5 or less, for example about 1.3 or less, or about 1.15 or less, or about 1.0 or less, or about 0.95 or less, or about 0.90 or less, or about 0.85 or less, or about 0.80 or less, or about 0.75 or less. Additionally or alternatively, the thermal ratio can be at least about 0.25, or at least about 0.35, or at least about 0.45, or at least about 0.50. Additionally or alternatively, in some aspects the fuel cell can be operated to have a temperature rise between anode input and anode output of about 40° C. or less, such as about 20° C. or less, or about 10° C. or less. Further additionally or alternatively, the fuel cell can be operated to have an anode outlet temperature that is from about 10° C. lower to about 10° C. higher than the temperature of the anode inlet. Still further additionally or alternatively, the fuel cell can be operated to have an anode inlet temperature that is greater than the anode outlet temperature, such as at least about 5° C. greater, or at least about 10° C. greater, or at least about 20° C. greater, or at least about 25° C. greater. Yet still further additionally or alternatively, the fuel cell can be operated to have an anode inlet temperature that is greater than the anode outlet temperature by about 100° C. or less, such as by about 80° C. or less, or about 60° C. or less, or about 50° C. or less, or about 40° C. or less, or about 30° C. or less, or about 20° C. or less.

As an addition, complement, and/or alternative to the fuel cell operating strategies described herein, a molten carbonate fuel cell (such as a fuel cell assembly) can be operated with increased production of syngas (or hydrogen) while also reducing or minimizing the amount of $CO_2$ exiting the fuel cell in the cathode exhaust stream. Syngas can be a valuable input for a variety of processes. In addition to having fuel value, syngas can be used as a raw material for forming other higher value products, such as by using syngas as an input for Fischer-Tropsch synthesis and/or methanol synthesis processes. One option for making syngas can be to reform a hydrocarbon or hydrocarbon-like fuel, such as methane or natural gas. For many types of industrial processes, a syngas having a ratio of $H_2$ to CO of close to 2:1 (or even lower) can often be desirable. A water gas shift reaction can be used to reduce the $H_2$ to CO ratio in a syngas if additional $CO_2$ is available, such as is produced in the anodes.

One way of characterizing the overall benefit provided by integrating syngas generation with use of molten carbonate fuel cells can be based on a ratio of the net amount of syngas that exits the fuel cells in the anode exhaust relative to the amount of $CO_2$ that exits the fuel cells in the cathode exhaust. This characterization measures the effectiveness of producing power with low emissions and high efficiency (both electrical and chemical). In this description, the net amount of syngas in an anode exhaust is defined as the combined number of moles of $H_2$ and number of moles of CO present in the anode exhaust, offset by the amount of $H_2$ and CO present in the anode inlet. Because the ratio is based on the net amount of syngas in the anode exhaust, simply passing excess $H_2$ into the anode does not change the value of the ratio. However, $H_2$ and/or CO generated due to reforming in the anode and/or in an internal reforming stage associated with the anode can lead to higher values of the ratio. Hydrogen oxidized in the anode can lower the ratio. It is noted that the water gas shift reaction can exchange $H_2$ for CO, so the combined moles of $H_2$ and CO represents the total potential syngas in the anode exhaust, regardless of the eventual desired ratio of $H_2$ to CO in a syngas. The syngas content of the anode exhaust ($H_2$+CO) can then be compared with the $CO_2$ content of the cathode exhaust. This can provide a type of efficiency value that can also account for the amount of carbon capture. This can equivalently be expressed as an equation as Ratio of net syngas in anode exhaust to cathode $CO_2$=net moles of $(H_2+CO)_{ANODE}$/moles of $(CO_2)_{CATHODE}$ In various aspects, the ratio of net moles of syngas in the anode exhaust to the moles of $CO_2$ in the cathode exhaust can be at least about 2.0, such as at least about 3.0, or at least about 4.0, or at least about 5.0. In some aspects, the ratio of net syngas in the anode exhaust to the amount of $CO_2$ in the cathode exhaust can be still higher, such as at least about 10.0, or at least about 15.0, or at least about 20.0. Ratio values of about 40.0 or less, such as about 30.0 or less, or about 20.0 or less, can additionally or alternately be achieved. In aspects where the amount of $CO_2$ at the cathode inlet is about 6.0 volume % or less, such as about 5.0 volume % or less, ratio values of at least about 1.5 may be sufficient/realistic. Such molar ratio values of net syngas in the anode exhaust to the amount of $CO_2$ in the cathode exhaust can be greater than the values for conventionally operated fuel cells.

As an addition, complement, and/or alternative to the fuel cell operating strategies described herein, a molten carbonate fuel cell (such as a fuel cell assembly) can be operated at a reduced fuel utilization value, such as a fuel utilization of about 50% or less, while also having a high $CO_2$ utilization value, such as at least about 60%. In this type of configuration, the molten carbonate fuel cell can be effective for carbon capture, as the $CO_2$ utilization can advantageously be sufficiently high. Rather than attempting to maximize electrical efficiency, in this type of configuration the total efficiency of the fuel cell can be improved or increased based on the combined electrical and chemical efficiency. The chemical efficiency can be based on withdrawal of a hydrogen and/or syngas stream from the anode exhaust as an output for use in other processes. Even though the electrical efficiency may be reduced relative to some conventional configurations, making use of the chemical energy output in the anode exhaust can allow for a desirable total efficiency for the fuel cell.

In various aspects, the fuel utilization in the fuel cell anode can be about 50% or less, such as about 40% or less, or about 30% or less, or about 25% or less, or about 20% or less. In various aspects, in order to generate at least some electric power, the fuel utilization in the fuel cell can be at least about 5%, such as at least about 10%, or at least about 15%, or at least about 20%, or at least about 25%, or at least about 30%. Additionally or alternatively, the $CO_2$ utilization can be at least about 60%, such as at least about 65%, or at least about 70%, or at least about 75%.

As an addition, complement, and/or alternative to the fuel cell operating strategies described herein, a molten carbonate fuel cell can be operated at conditions that increase or maximize syngas production, possibly at the detriment of electricity production and electrical efficiency. Instead of selecting the operating conditions of a fuel cell to improve or maximize the electrical efficiency of the fuel cell, operating conditions, possibly including an amount of reformable fuel passed into the anode, can be established to increase the chemical energy output of the fuel cell. These operating conditions can result in a lower electrical efficiency of the fuel cell. Despite the reduced electrical efficiency, optionally, but preferably, the operating conditions can lead to an increase in the total efficiency of the fuel cell, which is based on the combined electrical efficiency and chemical efficiency of the fuel cell. By increasing the ratio of reformable fuel introduced into the anode to the fuel that is actually electrochemically oxidized at the anode, the chemical energy content in the anode output can be increased.

In some aspects, the reformable hydrogen content of reformable fuel in the input stream delivered to the anode and/or to a reforming stage associated with the anode can be at least about 50% greater than the net amount of hydrogen reacted at the anode, such as at least about 75% greater or at least about 100% greater. Additionally or alternatively, the reformable hydrogen content of fuel in the input stream delivered to the anode and/or to a reforming stage associated with the anode can be at least about 50% greater than the net amount of hydrogen reacted at the anode, such as at least about 75% greater or at least about 100% greater. In various aspects, a ratio of the reformable hydrogen content of the reformable fuel in the fuel stream relative to an amount of hydrogen reacted in the anode can be at least about 1.5:1, or at least about 2.0:1, or at least about 2.5:1, or at least about 3.0:1. Additionally or alternatively, the ratio of reformable hydrogen content of the reformable fuel in the fuel stream relative to the amount of hydrogen reacted in the anode can be about 20:1 or less, such as about 15:1 or less or about 10:1 or less. In one aspect, it is contemplated that less than 100% of the reformable hydrogen content in the anode inlet stream can be converted to hydrogen. For example, at least about 80% of the reformable hydrogen content in an anode inlet stream can be converted to hydrogen in the anode and/or in an associated reforming stage(s), such as at least about 85%, or at least about 90%. Additionally or alternatively, the amount of reformable fuel delivered to the anode can be characterized based on the Lower Heating Value (LHV) of the reformable fuel relative to the LHV of the hydrogen oxidized in the anode. This can be referred to as a reformable fuel surplus ratio. In various aspects, the reformable fuel surplus ratio can be at least about 2.0, such as at least about 2.5, or at least about 3.0, or at least about 4.0. Additionally or alternately, the reformable fuel surplus ratio can be about 25.0 or less, such as about 20.0 or less, or about 15.0 or less, or about 10.0 or less.

As an addition, complement, and/or alternative to the fuel cell operating strategies described herein, a molten carbonate fuel cell (such as a fuel cell assembly) can also be operated at conditions that can improve or optimize the combined electrical efficiency and chemical efficiency of the fuel cell. Instead of selecting conventional conditions for maximizing the electrical efficiency of a fuel cell, the operating conditions can allow for output of excess synthesis gas and/or hydrogen in the anode exhaust of the fuel cell. The synthesis gas and/or hydrogen can then be used in a variety of applications, including chemical synthesis processes and collection of hydrogen for use as a "clean" fuel. In aspects of the invention, electrical efficiency can be reduced to achieve a high overall efficiency, which includes a chemical efficiency based on the chemical energy value of syngas and/or hydrogen produced relative to the energy value of the fuel input for the fuel cell.

In some aspects, the operation of the fuel cells can be characterized based on electrical efficiency. Where fuel cells are operated to have a low electrical efficiency (EE), a molten carbonate fuel cell can be operated to have an electrical efficiency of about 40% or less, for example, about 35% EE or less, about 30% EE or less, about 25% EE or less, or about 20% EE or less, about 15% EE or less, or about 10% EE or less. Additionally or alternately, the EE can be at least about 5%, or at least about 10%, or at least about 15%, or at least about 20%. Further additionally or alternately, the operation of the fuel cells can be characterized based on total fuel cell efficiency (TFCE), such as a combined electrical efficiency and chemical efficiency of the fuel cell(s). Where fuel cells are operated to have a high total fuel cell efficiency, a molten carbonate fuel cell can be operated to have a TFCE (and/or combined electrical efficiency and chemical efficiency) of about 55% or more, for example, about 60% or more, or about 65% or more, or about 70% or more, or about 75% or more, or about 80% or more, or about 85% or more. It is noted that for a total fuel cell efficiency and/or combined electrical efficiency and chemical efficiency, any additional electricity generated from use of excess heat generated by the fuel cell can be excluded from the efficiency calculation.

In various aspects of the invention, the operation of the fuel cells can be characterized based on a desired electrical efficiency of about 40% or less and a desired total fuel cell efficiency of about 55% or more. Where fuel cells are operated to have a desired electrical efficiency and a desired total fuel cell efficiency, a molten carbonate fuel cell can be operated to have an electrical efficiency of about 40% or less with a TFCE of about 55% or more, for example, about 35% EE or less with about a TFCE of 60% or more, about 30% EE or less with about a TFCE of about 65% or more, about 25% EE or less with about a 70% TFCE or more, or about 20% EE or less with about a TFCE of 75% or more, about 15% EE or less with about a TFCE of 80% or more, or about 10% EE or less with about a TFCE of about 85% or more.

As an addition, complement, and/or alternative to the fuel cell operating strategies described herein, a molten carbonate fuel cell (such as a fuel cell assembly) can be operated at conditions that can provide increased power density. The power density of a fuel cell corresponds to the actual operating voltage $V_A$ multiplied by the current density I. For a molten carbonate fuel cell operating at a voltage $V_A$, the fuel cell also can tend to generate waste heat, the waste heat defined as $(V_0-V_A)*I$ based on the differential between $V_A$ and the ideal voltage $V_0$ for a fuel cell providing current density I. A portion of this waste heat can be consumed by reforming of a reformable fuel within the anode of the fuel cell. The remaining portion of this waste heat can be absorbed by the surrounding fuel cell structures and gas flows, resulting in a temperature differential across the fuel cell. Under conventional operating conditions, the power density of a fuel cell can be limited based on the amount of waste heat that the fuel cell can tolerate without compromising the integrity of the fuel cell.

In various aspects, the amount of waste heat that a fuel cell can tolerate can be increased by performing an effective amount of an endothermic reaction within the fuel cell. One example of an endothermic reaction includes steam reforming of a reformable fuel within a fuel cell anode and/or in an associated reforming stage, such as an integrated reforming stage in a fuel cell stack. By providing additional reformable fuel to the anode of the fuel cell (or to an integrated/associated reforming stage), additional reforming can be performed so that additional waste heat can be consumed. This can reduce the amount of temperature differential across the fuel cell, thus allowing the fuel cell to operate under an operating condition with an increased amount of waste heat. The loss of electrical efficiency can be offset by the creation of an additional product stream, such as syngas and/or $H_2$, that can be used for various purposes including additional electricity generation further expanding the power range of the system.

In various aspects, the amount of waste heat generated by a fuel cell, $(V_0-V_A)*I$ as defined above, can be at least about 30 $mW/cm^2$, such as at least about 40 $mW/cm^2$, or at least about 50 $mW/cm^2$, or at least about 60 $mW/cm^2$, or at least about 70 $mW/cm^2$, or at least about 80 $mW/cm^2$, or at least about 100 $mW/cm^2$, or at least about 120 $mW/cm^2$, or at least about 140 $mW/cm^2$, or at least about 160 $mW/cm^2$, or at least about 180 $mW/cm^2$. Additionally or alternately, the amount of waste heat generated by a fuel cell can be less than about 250 $mW/cm^2$, such as less than about 200 $mW/cm^2$, or less than about 180 $mW/cm^2$, or less than about 165 $mW/cm^2$, or less than about 150 $mW/cm^2$.

Although the amount of waste heat being generated can be relatively high, such waste heat may not necessarily represent operating a fuel cell with poor efficiency. Instead, the waste heat can be generated due to operating a fuel cell at an increased power density. Part of improving the power density of a fuel cell can include operating the fuel cell at a sufficiently high current density. In various aspects, the current density generated by the fuel cell can be at least about 150 $mA/cm^2$, such as at least about 160 $mA/cm^2$, or at least about 170 $mA/cm^2$, or at least about 180 $mA/cm^2$, or at least about 190 $mA/cm^2$, or at least about 200 $mA/cm^2$, or at least about 225 $mA/cm^2$, or at least about 250 $mA/cm^2$. Additionally or alternately, the current density generated by the fuel cell can be about 500 $mA/cm^2$ or less, such as 450 $mA/cm^2$, or less, or 400 $mA/cm^2$, or less or 350 $mA/cm^2$, or less or 300 $mA/cm^2$ or less.

In various aspects, to allow a fuel cell to be operated with increased power generation and increased generation of waste heat, an effective amount of an endothermic reaction (such as a reforming reaction) can be performed. Alternatively, other endothermic reactions unrelated to anode operations can be used to utilize the waste heat by interspersing "plates" or stages into the fuel cell array that are in thermal communication but not fluid communication. The effective amount of the endothermic reaction can be performed in an associated reforming stage, an integrated reforming stage, an integrated stack element for performing an endothermic reaction, or a combination thereof. The effective amount of the endothermic reaction can correspond to an amount sufficient to reduce the temperature rise from the fuel cell inlet to the fuel cell outlet to about 100° C. or less, such as about 90° C. or less, or about 80° C. or less, or about 70° C. or less, or about 60° C. or less, or about 50° C. or less, or about 40° C. or less, or about 30° C. or less. Additionally or alternately, the effective amount of the endothermic reaction can correspond to an amount sufficient to cause a temperature decrease from the fuel cell inlet to the fuel cell outlet of about 100° C. or less, such as about 90° C. or less, or about 80° C. or less, or about 70° C. or less, or about 60° C. or less, or about 50° C. or less, or about 40° C. or less, or about 30° C. or less, or about 20° C. or less, or about 10° C. or less. A temperature decrease from the fuel cell inlet to the fuel cell outlet can occur when the effective amount of the endothermic reaction exceeds the waste heat generated. Additionally or alternately, this can correspond to having the endothermic reaction(s) (such as a combination of reforming and another endothermic reaction) consume at least about 40% of the waste heat generated by the fuel cell, such as consuming at least about 50% of the waste heat, or at least about 60% of the waste heat, or at least about 75% of the waste heat. Further additionally or alternately, the endothermic reaction(s) can consume about 95% of the waste heat or less, such as about 90% of the waste heat or less, or about 85% of the waste heat or less.

As an addition, complement, and/or alternative to the fuel cell operating strategies described herein, a molten carbonate fuel cell (such as a fuel cell assembly) can be operated at conditions corresponding to a decreased operating voltage and a low fuel utilization. In various aspects, the fuel cell can be operated at a voltage $V_A$ of less than about 0.7 Volts, for example less than about 0.68 V, less than about 0.67 V, less than about 0.66 V, or about 0.65 V or less. Additionally or alternately, the fuel cell can be operated at a voltage $V_A$ of at least about 0.60 V, for example at least about 0.61 V, at least about 0.62 V, or at least about 0.63 V. In so doing, energy that would otherwise leave the fuel cell as electrical energy at high voltage can remain within the cell as heat as the voltage is lowered. This additional heat can allow for increased endothermic reactions to occur, for example increasing the $CH_4$ conversion to syngas.

Definitions

Syngas: In this description, syngas is defined as mixture of $H_2$ and CO in any ratio. Optionally, $H_2O$ and/or $CO_2$ may be present in the syngas. Optionally, inert compounds (such as nitrogen) and residual reformable fuel compounds may be present in the syngas. If components other than $H_2$ and CO are present in the syngas, the combined volume percentage of $H_2$ and CO in the syngas can be at least 25 vol % relative to the total volume of the syngas, such as at least 40 vol %, or at least 50 vol %, or at least 60 vol %. Additionally or alternately, the combined volume percentage of $H_2$ and CO in the syngas can be 100 vol % or less, such as 95 vol % or less or 90 vol % or less.

Reformable fuel: A reformable fuel is defined as a fuel that contains carbon-hydrogen bonds that can be reformed to generate $H_2$. Hydrocarbons are examples of reformable fuels, as are other hydrocarbonaceous compounds such as alcohols. Although CO and $H_2O$ can participate in a water gas shift reaction to form hydrogen, CO is not considered a reformable fuel under this definition.

Reformable hydrogen content: The reformable hydrogen content of a fuel is defined as the number of $H_2$ molecules that can be derived from a fuel by reforming the fuel and then driving the water gas shift reaction to completion to maximize $H_2$ production. It is noted that $H_2$ by definition has a reformable hydrogen content of 1, although $H_2$ itself is not defined as a reformable fuel herein. Similarly, CO has a reformable hydrogen content of 1. Although CO is not strictly reformable, driving the water gas shift reaction to completion will result in exchange of a CO for an $H_2$. As examples of reformable hydrogen content for reformable fuels, the reformable hydrogen content of methane is $4H_2$ molecules while the reformable hydrogen content of ethane is $7H_2$ molecules. More generally, if a fuel has the composition $C_xH_yO_z$, then the reformable hydrogen content of the fuel at 100% reforming and water-gas shift is $n(H_2 \text{ max reforming})=2x+y/2-z$. Based on this definition, fuel utilization within a cell can then be expressed as $n(H_2 \text{ ox})/n(H_2 \text{ max reforming})$. Of course, the reformable hydrogen content of a mixture of components can be determined based on the reformable hydrogen content of the individual components. The reformable hydrogen content of compounds that contain other heteroatoms, such as oxygen, sulfur or nitrogen, can also be calculated in a similar manner.

Oxidation Reaction: In this discussion, the oxidation reaction within the anode of a fuel cell is defined as the reaction corresponding to oxidation of $H_2$ by reaction with $CO_3^{2-}$ to form $H_2O$ and $CO_2$. It is noted that the reforming reaction within the anode, where a compound containing a carbon-hydrogen bond is converted into $H_2$ and CO or $CO_2$, is excluded from this definition of the oxidation reaction in the anode. The water-gas shift reaction is similarly outside of this definition of the oxidation reaction. It is further noted that references to a combustion reaction are defined as references to reactions where $H_2$ or a compound containing carbon-hydrogen bond(s) are reacted with $O_2$ to form $H_2O$ and carbon oxides in a non-electrochemical burner, such as the combustion zone of a combustion-powered generator.

Aspects of the invention can adjust anode fuel parameters to achieve a desired operating range for the fuel cell. Anode fuel parameters can be characterized directly, and/or in relation to other fuel cell processes in the form of one or more ratios. For example, the anode fuel parameters can be controlled to achieve one or more ratios including a fuel utilization, a fuel cell heating value utilization, a fuel surplus ratio, a reformable fuel surplus ratio, a reformable hydrogen content fuel ratio, and combinations thereof.

Fuel utilization: Fuel utilization is an option for characterizing operation of the anode based on the amount of oxidized fuel relative to the reformable hydrogen content of an input stream can be used to define a fuel utilization for a fuel cell. In this discussion, "fuel utilization" is defined as the ratio of the amount of hydrogen oxidized in the anode for production of electricity (as described above) versus the reformable hydrogen content of the anode input (including any associated reforming stages). Reformable hydrogen content has been defined above as the number of $H_2$ molecules that can be derived from a fuel by reforming the fuel and then driving the water gas shift reaction to completion to maximize $H_2$ production. For example, each methane introduced into an anode and exposed to steam reforming conditions results in generation of the equivalent of $4H_2$ molecules at max production. (Depending on the reforming and/or anode conditions, the reforming product can correspond to a non-water gas shifted product, where one or more of the $H_2$ molecules is present instead in the form of a CO molecule.) Thus, methane is defined as having a reformable hydrogen content of $4H_2$ molecules. As another example, under this definition ethane has a reformable hydrogen content of $7H_2$ molecules.

The utilization of fuel in the anode can also be characterized by defining a heating value utilization based on a ratio of the Lower Heating Value of hydrogen oxidized in the anode due to the fuel cell anode reaction relative to the Lower Heating Value of all fuel delivered to the anode and/or a reforming stage associated with the anode. The "fuel cell heating value utilization" as used herein can be computed using the flow rates and Lower Heating Value (LHV) of the fuel components entering and leaving the fuel cell anode. As such, fuel cell heating value utilization can be computed as (LHV(anode_in)−LHV(anode out))/LHV(anode_in), where LHV(anode_in) and LHV(anode out) refer to the LHV of the fuel components (such as $H_2$, $CH_4$, and/or CO) in the anode inlet and outlet streams or flows, respectively. In this definition, the LHV of a stream or flow may be computed as a sum of values for each fuel component in the input and/or output stream. The contribution of each fuel component to the sum can correspond to the fuel component's flow rate (e.g., mol/hr) multiplied by the fuel component's LHV (e.g., joules/mol).

Lower Heating Value: The lower heating value is defined as the enthalpy of combustion of a fuel component to vapor phase, fully oxidized products (i.e., vapor phase $CO_2$ and $H_2O$ product). For example, any $CO_2$ present in an anode input stream does not contribute to the fuel content of the anode input, since $CO_2$ is already fully oxidized. For this definition, the amount of oxidation occurring in the anode due to the anode fuel cell reaction is defined as oxidation of $H_2$ in the anode as part of the electrochemical reaction in the anode, as defined above.

It is noted that, for the special case where the only fuel in the anode input flow is $H_2$, the only reaction involving a fuel component that can take place in the anode represents the conversion of $H_2$ into $H_2O$. In this special case, the fuel utilization simplifies to ($H_2$-rate-in minus $H_2$-rate-out)/$H_2$-rate-in. In such a case, $H_2$ would be the only fuel component, and so the $H_2$ LHV would cancel out of the equation. In the more general case, the anode feed may contain, for example, $CH_4$, $H_2$, and CO in various amounts. Because these species can typically be present in different amounts in the anode outlet, the summation as described above can be needed to determine the fuel utilization.

Alternatively or in addition to fuel utilization, the utilization for other reactants in the fuel cell can be characterized. For example, the operation of a fuel cell can additionally or alternately be characterized with regard to "$CO_2$ utilization" and/or "oxidant" utilization. The values for $CO_2$ utilization and/or oxidant utilization can be specified in a similar manner.

Fuel surplus ratio: Still another way to characterize the reactions in a molten carbonate fuel cell is by defining a utilization based on a ratio of the Lower Heating Value of all fuel delivered to the anode and/or a reforming stage associated with the anode relative to the Lower Heating Value of hydrogen oxidized in the anode due to the fuel cell anode reaction. This quantity will be referred to as a fuel surplus ratio. As such the fuel surplus ratio can be computed as (LHV (anode_in)/(LHV(anode_in)−LHV(anode_out)) where LHV(anode_in) and LHV(anode_out) refer to the LHV of the fuel components (such as $H_2$, $CH_4$, and/or CO) in the anode inlet and outlet streams or flows, respectively. In various aspects of the invention, a molten carbonate fuel cell can be operated to have a fuel surplus ratio of at least about 1.0, such as at least about 1.5, or at least about 2.0, or at least about 2.5, or at least about 3.0, or at least about 4.0. Additionally or alternately, the fuel surplus ratio can be about 25.0 or less.

It is noted that not all of the reformable fuel in the input stream for the anode may be reformed. Preferably, at least about 90% of the reformable fuel in the input stream to the anode (and/or into an associated reforming stage) can be reformed prior to exiting the anode, such as at least about 95% or at least about 98%. In some alternative aspects, the amount of reformable fuel that is reformed can be from about 75% to about 90%, such as at least about 80%.

The above definition for fuel surplus ratio provides a method for characterizing the amount of reforming occurring within the anode and/or reforming stage(s) associated with a fuel cell relative to the amount of fuel consumed in the fuel cell anode for generation of electric power.

Optionally, the fuel surplus ratio can be modified to account for situations where fuel is recycled from the anode output to the anode input. When fuel (such as $H_2$, CO, and/or unreformed or partially reformed hydrocarbons) is recycled from anode output to anode input, such recycled fuel components do not represent a surplus amount of reformable or reformed fuel that can be used for other purposes. Instead, such recycled fuel components merely indicate a desire to reduce fuel utilization in a fuel cell.

Reformable fuel surplus ratio: Calculating a reformable fuel surplus ratio is one option to account for such recycled fuel components is to narrow the definition of surplus fuel, so that only the LHV of reformable fuels is included in the input stream to the anode. As used herein the "reformable fuel surplus ratio" is defined as the Lower Heating Value of reformable fuel delivered to the anode and/or a reforming stage associated with the anode relative to the Lower Heating Value of hydrogen oxidized in the anode due to the fuel cell anode reaction. Under the definition for reformable fuel surplus ratio, the LHV of any $H_2$ or CO in the anode input is excluded. Such an LHV of reformable fuel can still be measured by characterizing the actual composition entering a fuel cell anode, so no distinction between recycled components and fresh components needs to be made. Although some non-reformed or partially reformed fuel may also be recycled, in most aspects the majority of the fuel recycled to the anode can correspond to reformed products such as $H_2$ or CO. Expressed mathematically, the reformable fuel surplus ratio $(R_{RFS})=LHV_{RF}/LHV_{OH}$, where $LHV_{RF}$ is the Lower Heating Value (LHV) of the reformable fuel and $LHV_{OH}$ is the Lower Heating Value (LHV) of the hydrogen oxidized in the anode. The LHV of the hydrogen oxidized in the anode may be calculated by subtracting the LHV of the anode outlet stream from the LHV of the anode inlet stream (e.g., LHV(anode_in)−LHV(anode_out)). In various aspects of the invention, a molten carbonate fuel cell can be operated to have a reformable fuel surplus ratio of at least about 0.25, such as at least about 0.5, or at least about 1.0, or at least about 1.5, or at least about 2.0, or at least about 2.5, or at least about 3.0, or at least about 4.0. Additionally or alternately, the reformable fuel surplus ratio can be about 25.0 or less. It is noted that this narrower definition based on the amount of reformable fuel delivered to the anode relative to the amount of oxidation in the anode can distinguish between two types of fuel cell operation methods that have low fuel utilization. Some fuel cells achieve low fuel utilization by recycling a substantial portion of the anode output back to the anode input. This recycle can allow any hydrogen in the anode input to be used again as an input to the anode. This can reduce the amount of reforming, as even though the fuel utilization is low for a single pass through the fuel cell, at least a portion of the unused fuel is recycled for use in a later pass. Thus, fuel cells with a wide variety of fuel utilization values may have the same ratio of reformable fuel delivered to the anode reforming stage(s) versus hydrogen oxidized in the anode reaction. In order to change the ratio of reformable fuel delivered to the anode reforming stages relative to the amount of oxidation in the anode, either an anode feed with a native content of non-reformable fuel needs to be identified, or unused fuel in the anode output needs to be withdrawn for other uses, or both.

Reformable hydrogen surplus ratio: Still another option for characterizing the operation of a fuel cell is based on a "reformable hydrogen surplus ratio." The reformable fuel surplus ratio defined above is defined based on the lower heating value of reformable fuel components. The reformable hydrogen surplus ratio is defined as the reformable hydrogen content of reformable fuel delivered to the anode and/or a reforming stage associated with the anode relative to the hydrogen reacted in the anode due to the fuel cell anode reaction. As such, the "reformable hydrogen surplus ratio" can be computed as (RFC(reformable_anode_in)/ (RFC(reformable anode in)−RFC(anode_out)), where RFC (reformable anode_in) refers to the reformable hydrogen content of reformable fuels in the anode inlet streams or flows, while RFC (anode_out) refers to the reformable hydrogen content of the fuel components (such as $H_2$, $CH_4$, and/or CO) in the anode inlet and outlet streams or flows. The RFC can be expressed in moles/s, moles/hr, or similar. An example of a method for operating a fuel cell with a large ratio of reformable fuel delivered to the anode reforming stage(s) versus amount of oxidation in the anode can be a method where excess reforming is performed in order to balance the generation and consumption of heat in the fuel cell. Reforming a reformable fuel to form $H_2$ and CO is an endothermic process. This endothermic reaction can be countered by the generation of electrical current in the fuel cell, which can also produce excess heat corresponding (roughly) to the difference between the amount of heat generated by the anode oxidation reaction and the carbonate formation reaction and the energy that exits the fuel cell in the form of electric current. The excess heat per mole of hydrogen involved in the anode oxidation reaction/carbonate formation reaction can be greater than the heat absorbed to generate a mole of hydrogen by reforming. As a result, a fuel cell operated under conventional conditions can exhibit a temperature increase from inlet to outlet. Instead of this type of conventional operation, the amount of fuel reformed in the reforming stages associated with the anode can be increased. For example, additional fuel can be reformed so that the heat generated by the exothermic fuel cell reactions can be (roughly) balanced by the heat consumed in reforming, or even the heat consumed by reforming can be beyond the excess heat generated by the fuel oxidation, resulting in a temperature drop across the fuel cell. This can result in a substantial excess of hydrogen relative to the amount needed for electrical power generation. As one example, a feed to the anode inlet of a fuel cell or an associated reforming stage can be substantially composed of reformable fuel, such as a substantially pure methane feed. During conventional operation for electric power generation using such a fuel, a molten carbonate fuel cell can be operated with a fuel utilization of about 75%. This means that about 75% (or ¾) of the fuel content delivered to the anode is used to form hydrogen that is then reacted in the anode with carbonate ions to form $H_2O$ and $CO_2$. In conventional operation, the remaining about 25% of the fuel content can be reformed to $H_2$ within the fuel cell (or can pass through the fuel cell unreacted for any CO or $H_2$ in the fuel), and then combusted outside of the fuel cell to form $H_2O$ and $CO_2$ to provide heat for the cathode inlet to the fuel cell. The reformable hydrogen surplus ratio in this situation can be 4/(4−1)=4/3.

Electrical efficiency: As used herein, the term "electrical efficiency" ("EE") is defined as the electrochemical power produced by the fuel cell divided by the rate of Lower Heating Value ("LHV") of fuel input to the fuel cell. The fuel inputs to the fuel cell includes both fuel delivered to the anode as well as any fuel used to maintain the temperature of the fuel cell, such as fuel delivered to a burner associated with a fuel cell. In this description, the power produced by the fuel may be described in terms of LHV(el) fuel rate.

Electrochemical power: As used herein, the term "electrochemical power" or LHV(el) is the power generated by the circuit connecting the cathode to the anode in the fuel cell and the transfer of carbonate ions across the fuel cell's electrolyte. Electrochemical power excludes power produced or consumed by equipment upstream or downstream from the fuel cell. For example, electricity produced from heat in a fuel cell exhaust stream is not considered part of the electrochemical power. Similarly, power generated by a gas turbine or other equipment upstream of the fuel cell is not part of the electrochemical power generated. The "electrochemical power" does not take electrical power consumed during operation of the fuel cell into account, or any loss incurred by conversion of the direct current to alternating current. In other words, electrical power used to supply the fuel cell operation or otherwise operate the fuel cell is not subtracted from the direct current power produced by the fuel cell. As used herein, the power density is the current density multiplied by voltage. As used herein, the total fuel cell power is the power density multiplied by the fuel cell area.

Fuel inputs: As used herein, the term "anode fuel input," designated as LHV(anode_in), is the amount of fuel within the anode inlet stream. The term "fuel input", designated as LHV(in), is the total amount of fuel delivered to the fuel cell, including both the amount of fuel within the anode inlet stream and the amount of fuel used to maintain the temperature of the fuel cell. The fuel may include both reformable and nonreformable fuels, based on the definition of a reformable fuel provided herein. Fuel input is not the same as fuel utilization.

Total fuel cell efficiency: As used herein, the term "total fuel cell efficiency" ("TFCE") is defined as: the electrochemical power generated by the fuel cell, plus the rate of LHV of syngas produced by the fuel cell, divided by the rate of LHV of fuel input to the anode. In other words, TFCE= (LHV(el)+LHV(sg net))/LHV(anode_in), where LHV(anode_in) refers to rate at which the LHV of the fuel components (such as $H_2$, $CH_4$, and/or CO) delivered to the anode and LHV(sg net) refers to a rate at which syngas ($H_2$, CO) is produced in the anode, which is the difference between syngas input to the anode and syngas output from the anode. LHV(el) describes the electrochemical power generation of the fuel cell. The total fuel cell efficiency excludes heat generated by the fuel cell that is put to beneficial use outside of the fuel cell. In operation, heat generated by the fuel cell may be put to beneficial use by downstream equipment. For example, the heat may be used to generate additional electricity or to heat water. These uses, when they occur apart from the fuel cell, are not part of the total fuel cell efficiency, as the term is used in this application. The total fuel cell efficiency is for the fuel cell operation only, and does not include power production, or consumption, upstream, or downstream, of the fuel cell.

Chemical efficiency: As used herein, the term "chemical efficiency", is defined as the lower heating value of $H_2$ and CO in the anode exhaust of the fuel cell, or LHV(sg out), divided by the fuel input, or LHV(in).

Neither the electrical efficiency nor the total system efficiency takes the efficiency of upstream or downstream processes into consideration. For example, it may be advantageous to use turbine exhaust as a source of $CO_2$ for the fuel cell cathode. In this arrangement, the efficiency of the turbine is not considered as part of the electrical efficiency or the total fuel cell efficiency calculation. Similarly, outputs from the fuel cell may be recycled as inputs to the fuel cell. A recycle loop is not considered when calculating electrical efficiency or the total fuel cell efficiency in single pass mode.

Syngas produced: As used herein, the term "syngas produced" is the difference between syngas input to the anode and syngas output from the anode. Syngas may be used as an input, or fuel, for the anode, at least in part. For example, a system may include an anode recycle loop that returns syngas from the anode exhaust to the anode inlet where it is supplemented with natural gas or other suitable fuel. Syngas produced LHV (sg net)=(LHV(sg out)−LHV(sg in)), where LHV(sg in) and LHV(sg out) refer to the LHV of the syngas in the anode inlet and syngas in the anode outlet streams or flows, respectively. It is noted that at least a portion of the syngas produced by the reforming reactions within an anode can typically be utilized in the anode to produce electricity. The hydrogen utilized to produce electricity is not included in the definition of "syngas produced" because it does not exit the anode. As used herein, the term "syngas ratio" is the LHV of the net syngas produced divided by the LHV of the fuel input to the anode or LHV (sg net)/LHV(anode in). Molar flow rates of syngas and fuel can be used instead of LHV to express a molar-based syngas ratio and a molar-based syngas produced.

Steam to carbon ratio (S/C): As used herein, the steam to carbon ratio (S/C) is the molar ratio of steam in a flow to reformable carbon in the flow. Carbon in the form of CO and $CO_2$ are not included as reformable carbon in this definition. The steam to carbon ratio can be measured and/or controlled at different points in the system. For example, the composition of an anode inlet stream can be manipulated to achieve a S/C that is suitable for reforming in the anode. The S/C can be given as the molar flow rate of $H_2O$ divided by the product of the molar flow rate of fuel multiplied by the number of carbon atoms in the fuel, e.g. one for methane. Thus, S/C=$f_{H2O}(f_{CH4}$ X#C), where $f_{H2O}$ is the molar flow rate of water, where $f_{CH4}$ is the molar flow rate of methane (or other fuel) and #C is the number of carbons in the fuel.

EGR ratio: Aspects of the invention can use a turbine in partnership with a fuel cell. The combined fuel cell and turbine system may include exhaust gas recycle ("EGR"). In an EGR system, at least a portion of the exhaust gas generated by the turbine can be sent to a heat recovery generator. Another portion of the exhaust gas can be sent to the fuel cell. The EGR ratio describes the amount of exhaust gas routed to the fuel cell versus the total exhaust gas routed to either the fuel cell or heat recovery generator. As used herein, the "EGR ratio" is the flow rate for the fuel cell bound portion of the exhaust gas divided by the combined flow rate for the fuel cell bound portion and the recovery bound portion, which is sent to the heat recovery generator.

In various aspects of the invention, a molten carbonate fuel cell (MCFC) can be used to facilitate separation of $CO_2$ from a $CO_2$-containing stream while also generating additional electrical power. The $CO_2$ separation can be further enhanced by taking advantage of synergies with the combustion-based power generator that can provide at least a portion of the input feed to the cathode portion of the fuel cell.

Fuel Cell and Fuel Cell Components: In this discussion, a fuel cell can correspond to a single cell, with an anode and a cathode separated by an electrolyte. The anode and cathode can receive input gas flows to facilitate the respective anode and cathode reactions for transporting charge across the electrolyte and generating electricity. A fuel cell stack can represent a plurality of cells in an integrated unit. Although a fuel cell stack can include multiple fuel cells, the fuel cells can typically be connected in parallel and can function (approximately) as if they collectively represented a single fuel cell of a larger size. When an input flow is delivered to the anode or cathode of a fuel cell stack, the fuel stack can include flow channels for dividing the input flow between each of the cells in the stack and flow channels for combining the output flows from the individual cells. In this discussion, a fuel cell array can be used to refer to a plurality of fuel cells (such as a plurality of fuel cell stacks) that are arranged in series, in parallel, or in any other convenient manner (e.g., in a combination of series and parallel). A fuel cell array can include one or more stages of fuel cells and/or fuel cell stacks, where the anode/cathode output from a first stage may serve as the anode/cathode input for a second stage. It is noted that the anodes in a fuel cell array do not have to be connected in the same way as the cathodes in the array. For convenience, the input to the first anode stage of a fuel cell array may be referred to as the anode input for the array, and the input to the first cathode stage of the fuel cell array may be referred to as the cathode input to the array. Similarly, the output from the final anode/cathode stage may be referred to as the anode/cathode output from the array.

It should be understood that reference to use of a fuel cell herein typically denotes a "fuel cell stack" composed of individual fuel cells, and more generally refers to use of one or more fuel cell stacks in fluid communication. Individual fuel cell elements (plates) can typically be "stacked" together in a rectangular array called a "fuel cell stack". This fuel cell stack can typically take a feed stream and distribute reactants among all of the individual fuel cell elements and can then collect the products from each of these elements. When viewed as a unit, the fuel cell stack in operation can be taken as a whole even though composed of many (often tens or hundreds) of individual fuel cell elements. These individual fuel cell elements can typically have similar voltages (as the reactant and product concentrations are similar), and the total power output can result from the summation of all of the electrical currents in all of the cell elements, when the elements are electrically connected in series. Stacks can also be arranged in a series arrangement to produce high voltages. A parallel arrangement can boost the current. If a sufficiently large volume fuel cell stack is available to process a given exhaust flow, the systems and methods described herein can be used with a single molten carbonate fuel cell stack. In other aspects of the invention, a plurality of fuel cell stacks may be desirable or needed for a variety of reasons.

For the purposes of this invention, unless otherwise specified, the term "fuel cell" should be understood to also refer to and/or is defined as including a reference to a fuel cell stack composed of set of one or more individual fuel cell elements for which there is a single input and output, as that is the manner in which fuel cells are typically employed in practice. Similarly, the term fuel cells (plural), unless otherwise specified, should be understood to also refer to and/or is defined as including a plurality of separate fuel cell stacks. In other words, all references within this document, unless specifically noted, can refer interchangeably to the operation of a fuel cell stack as a "fuel cell". For example, the volume of exhaust generated by a commercial scale combustion generator may be too large for processing by a fuel cell (i.e., a single stack) of conventional size. In order to process the full exhaust, a plurality of fuel cells (i.e., two or more separate fuel cells or fuel cell stacks) can be arranged in parallel, so that each fuel cell can process (roughly) an equal portion of the combustion exhaust. Although multiple fuel cells can be used, each fuel cell can typically be operated in a generally similar manner, given its (roughly) equal portion of the combustion exhaust.

"Internal reforming" and "external reforming": A fuel cell or fuel cell stack may include one or more internal reforming sections. As used herein, the term "internal reforming" refers to fuel reforming occurring within the body of a fuel cell, a fuel cell stack, or otherwise within a fuel cell assembly. External reforming, which is often used in conjunction with a fuel cell, occurs in a separate piece of equipment that is located outside of the fuel cell stack. In other words, the body of the external reformer is not in direct physical contact with the body of a fuel cell or fuel cell stack. In a typical set up, the output from the external reformer can be fed to the anode inlet of a fuel cell. Unless otherwise noted specifically, the reforming described within this application is internal reforming.

Internal reforming may occur within a fuel cell anode. Internal reforming can additionally or alternately occur within an internal reforming element integrated within a fuel cell assembly. The integrated reforming element may be located between fuel cell elements within a fuel cell stack. In other words, one of the trays in the stack can be a reforming section instead of a fuel cell element. In one aspect, the flow arrangement within a fuel cell stack directs fuel to the internal reforming elements and then into the anode portion of the fuel cells. Thus, from a flow perspective, the internal reforming elements and fuel cell elements can be arranged in series within the fuel cell stack. As used herein, the term "anode reforming" is fuel reforming that occurs within an anode. As used herein, the term "internal reforming" is reforming that occurs within an integrated reforming element and not in an anode section.

In some aspects, a reforming stage that is internal to a fuel cell assembly can be considered to be associated with the anode(s) in the fuel cell assembly. In some alternative aspects, for a reforming stage in a fuel cell stack that can be associated with an anode (such as associated with multiple anodes), a flow path can be available so that the output flow from the reforming stage is passed into at least one anode. This can correspond to having an initial section of a fuel cell plate not in contact with the electrolyte and instead can serve just as a reforming catalyst. Another option for an associated reforming stage can be to have a separate integrated reforming stage as one of the elements in a fuel cell stack, where the output from the integrated reforming stage can be returned to the input side of one or more of the fuel cells in the fuel cell stack.

From a heat integration standpoint, a characteristic height in a fuel cell stack can be the height of an individual fuel cell stack element. It is noted that the separate reforming stage and/or a separate endothermic reaction stage could have a different height in the stack than a fuel cell. In such a scenario, the height of a fuel cell element can be used as the characteristic height. In some aspects, an integrated endothermic reaction stage can be defined as a stage that is heat integrated with one or more fuel cells, so that the integrated endothermic reaction stage can use the heat from the fuel cells as a heat source for the endothermic reaction. Such an integrated endothermic reaction stage can be defined as being positioned less than 5 times the height of a stack element from any fuel cells providing heat to the integrated stage. For example, an integrated endothermic reaction stage (such as a reforming stage) can be positioned less than 5 times the height of a stack element from any fuel cells that are heat integrated, such as less than 3 times the height of a stack element. In this discussion, an integrated reforming stage and/or integrated endothermic reaction stage that represent an adjacent stack element to a fuel cell element can be defined as being about one stack element height or less away from the adjacent fuel cell element.

In some aspects, a separate reforming stage that is heat integrated with a fuel cell element can correspond to a reforming stage associated with the fuel cell element. In such aspects, an integrated fuel cell element can provide at least a portion of the heat to the associated reforming stage, and the associated reforming stage can provide at least a portion of the reforming stage output to the integrated fuel cell as a fuel stream. In other aspects, a separate reforming stage can be integrated with a fuel cell for heat transfer without being associated with the fuel cell. In this type of situation, the separate reforming stage can receive heat from the fuel cell, but the decision can be made not to use the output of the reforming stage as an input to the fuel cell. Instead, the decision can be made to use the output of such a reforming stage for another purpose, such as directly adding the output to the anode exhaust stream, and/or for forming a separate output stream from the fuel cell assembly.

More generally, a separate stack element in a fuel cell stack can be used to perform any convenient type of endothermic reaction that can take advantage of the waste heat provided by integrated fuel cell stack elements. Instead of plates suitable for performing a reforming reaction on a hydrocarbon fuel stream, a separate stack element can have plates suitable for catalyzing another type of endothermic reaction. A manifold or other arrangement of inlet conduits in the fuel cell stack can be used to provide an appropriate input flow to each stack element. A similar manifold or other arrangement of outlet conduits can additionally or alternately be used to withdraw the output flows from each stack element. Optionally, the output flows from a endothermic reaction stage in a stack can be withdrawn from the fuel cell stack without having the output flow pass through a fuel cell anode. In such an optional aspect, the products of the exothermic reaction can therefore exit from the fuel cell stack without passing through a fuel cell anode. Examples of other types of endothermic reactions that can be performed in stack elements in a fuel cell stack can include, without limitation, ethanol dehydration to form ethylene and ethane cracking.

Recycle: As defined herein, recycle of a portion of a fuel cell output (such as an anode exhaust or a stream separated or withdrawn from an anode exhaust) to a fuel cell inlet can correspond to a direct or indirect recycle stream. A direct recycle of a stream to a fuel cell inlet is defined as recycle of the stream without passing through an intermediate process, while an indirect recycle involves recycle after passing a stream through one or more intermediate processes. For example, if the anode exhaust is passed through a $CO_2$ separation stage prior to recycle, this is considered an indirect recycle of the anode exhaust. If a portion of the anode exhaust, such as an $H_2$ stream withdrawn from the anode exhaust, is passed into a gasifier for converting coal into a fuel suitable for introduction into the fuel cell, then that is also considered an indirect recycle.

Anode Inputs and Outputs

In various aspects of the invention, the MCFC array can be fed by a fuel received at the anode inlet that comprises, for example, both hydrogen and a hydrocarbon such as methane (or alternatively a hydrocarbonaceous or hydrocarbon-like compound that may contain heteroatoms different from C and H). Most of the methane (or other hydrocarbonaceous or hydrocarbon-like compound) fed to the anode can typically be fresh methane. In this description, a fresh fuel such as fresh methane refers to a fuel that is not recycled from another fuel cell process. For example, methane recycled from the anode outlet stream back to the anode inlet may not be considered "fresh" methane, and can instead be described as reclaimed methane. The fuel source used can be shared with other components, such as a turbine that uses a portion of the fuel source to provide a $CO_2$-containing stream for the cathode input. The fuel source input can include water in a proportion to the fuel appropriate for reforming the hydrocarbon (or hydrocarbon-like) compound in the reforming section that generates hydrogen. For example, if methane is the fuel input for reforming to generate $H_2$, the molar ratio of water to fuel can be from about one to one to about ten to one, such as at least about two to one. A ratio of four to one or greater is typical for external reforming, but lower values can be typical for internal reforming. To the degree that $H_2$ is a portion of the fuel source, in some optional aspects no additional water may be needed in the fuel, as the oxidation of $H_2$ at the anode can tend to produce $H_2O$ that can be used for reforming the fuel. The fuel source can also optionally contain components incidental to the fuel source (e.g., a natural gas feed can contain some content of $CO_2$ as an additional component). For example, a natural gas feed can contain $CO_2$, $N_2$, and/or other inert (noble) gases as additional components. Optionally, in some aspects the fuel source may also contain CO, such as CO from a recycled portion of the anode exhaust. An additional or alternate potential source for CO in the fuel into a fuel cell assembly can be CO generated by steam reforming of a hydrocarbon fuel performed on the fuel prior to entering the fuel cell assembly.

More generally, a variety of types of fuel streams may be suitable for use as an input stream for the anode of a molten carbonate fuel cell. Some fuel streams can correspond to streams containing hydrocarbons and/or hydrocarbon-like compounds that may also include heteroatoms different from C and H. In this discussion, unless otherwise specified, a reference to a fuel stream containing hydrocarbons for an MCFC anode is defined to include fuel streams containing such hydrocarbon-like compounds. Examples of hydrocarbon (including hydrocarbon-like) fuel streams include natural gas, streams containing C1-C4 carbon compounds (such as methane or ethane), and streams containing heavier C5+ hydrocarbons (including hydrocarbon-like compounds), as well as combinations thereof. Still other additional or alternate examples of potential fuel streams for use in an anode input can include biogas-type streams, such as methane produced from natural (biological) decomposition of organic material.

In some aspects, a molten carbonate fuel cell can be used to process an input fuel stream, such as a natural gas and/or hydrocarbon stream, with a low energy content due to the presence of diluent compounds. For example, some sources of methane and/or natural gas are sources that can include substantial amounts of either $CO_2$ or other inert molecules, such as nitrogen, argon, or helium. Due to the presence of elevated amounts of $CO_2$ and/or inerts, the energy content of a fuel stream based on the source can be reduced. Using a low energy content fuel for a combustion reaction (such as for powering a combustion-powered turbine) can pose difficulties. However, a molten carbonate fuel cell can generate power based on a low energy content fuel source with a reduced or minimal impact on the efficiency of the fuel cell. The presence of additional gas volume can require additional heat for raising the temperature of the fuel to the temperature for reforming and/or the anode reaction. Additionally, due to the equilibrium nature of the water gas shift reaction within a fuel cell anode, the presence of additional $CO_2$ can have an impact on the relative amounts of $H_2$ and CO present in the anode output. However, the inert compounds otherwise can have only a minimal direct impact on the reforming and anode reactions. The amount of $CO_2$ and/or inert compounds in a fuel stream for a molten carbonate fuel cell, when present, can be at least about 1 vol %, such as at least about 2 vol %, or at least about 5 vol %, or at least about 10 vol %, or at least about 15 vol %, or at least about 20 vol %, or at least about 25 vol %, or at least about 30 vol %, or at least about 35 vol %, or at least about 40 vol %, or at least about 45 vol %, or at least about 50 vol %, or at least about 75 vol %. Additionally or alternately, the amount of $CO_2$ and/or inert compounds in a fuel stream for a molten carbonate fuel cell can be about 90 vol % or less, such as about 75 vol % or less, or about 60 vol % or less, or about 50 vol % or less, or about 40 vol % or less, or about 35 vol % or less.

Yet other examples of potential sources for an anode input stream can correspond to refinery and/or other industrial process output streams. For example, coking is a common process in many refineries for converting heavier compounds to lower boiling ranges. Coking typically produces an off-gas containing a variety of compounds that are gases at room temperature, including CO and various C1-C4 hydrocarbons. This off-gas can be used as at least a portion of an anode input stream. Other refinery off-gas streams can additionally or alternately be suitable for inclusion in an anode input stream, such as light ends (C1-C4) generated during cracking or other refinery processes. Still other suitable refinery streams can additionally or alternately include refinery streams containing CO or $CO_2$ that also contain $H_2$ and/or reformable fuel compounds.

Still other potential sources for an anode input can additionally or alternately include streams with increased water content. For example, an ethanol output stream from an ethanol plant (or another type of fermentation process) can include a substantial portion of $H_2O$ prior to final distillation. Such $H_2O$ can typically cause only minimal impact on the operation of a fuel cell. Thus, a fermentation mixture of alcohol (or other fermentation product) and water can be used as at least a portion of an anode input stream.

Biogas, or digester gas, is another additional or alternate potential source for an anode input. Biogas may primarily comprise methane and $CO_2$ and is typically produced by the breakdown or digestion of organic matter. Anaerobic bacteria may be used to digest the organic matter and produce the biogas. Impurities, such as sulfur-containing compounds, may be removed from the biogas prior to use as an anode input.

The output stream from an MCFC anode can include $H_2O$, $CO_2$, CO, and $H_2$. Optionally, the anode output stream could also have unreacted fuel (such as $H_2$ or $CH_4$) or inert compounds in the feed as additional output components. Instead of using this output stream as a fuel source to provide heat for a reforming reaction or as a combustion fuel for heating the cell, one or more separations can be performed on the anode output stream to separate the $CO_2$ from the components with potential value as inputs to another process, such as $H_2$ or CO. The $H_2$ and/or CO can be used as a syngas for chemical synthesis, as a source of hydrogen for chemical reaction, and/or as a fuel with reduced greenhouse gas emissions.

In various aspects, the composition of the output stream from the anode can be impacted by several factors. Factors that can influence the anode output composition can include the composition of the input stream to the anode, the amount of current generated by the fuel cell, and/or the temperature at the exit of the anode. The temperature of at the anode exit can be relevant due to the equilibrium nature of the water gas shift reaction. In a typical anode, at least one of the plates forming the wall of the anode can be suitable for catalyzing the water gas shift reaction. As a result, if a) the composition of the anode input stream is known, b) the extent of reforming of reformable fuel in the anode input stream is known, and c) the amount of carbonate transported from the cathode to anode (corresponding to the amount of electrical current generated) is known, the composition of the anode output can be determined based on the equilibrium constant for the water gas shift reaction.

$K_{eq}=[CO_2][H_2]/[CO][H_2O]$

In the above equation, $K_{eq}$ is the equilibrium constant for the reaction at a given temperature and pressure, and [X] is the partial pressure of component X. Based on the water gas shift reaction, it can be noted that an increased $CO_2$ concentration in the anode input can tend to result in additional CO formation (at the expense of $H_2$) while an increased $H_2O$ concentration can tend to result in additional $H_2$ formation (at the expense of CO).

To determine the composition at the anode output, the composition of the anode input can be used as a starting point. This composition can then be modified to reflect the extent of reforming of any reformable fuels that can occur within the anode. Such reforming can reduce the hydrocarbon content of the anode input in exchange for increased hydrogen and $CO_2$. Next, based on the amount of electrical current generated, the amount of $H_2$ in the anode input can be reduced in exchange for additional $H_2O$ and $CO_2$. This composition can then be adjusted based on the equilibrium constant for the water gas shift reaction to determine the exit concentrations for $H_2$, CO, $CO_2$, and $H_2O$.

Table 1 shows the anode exhaust composition at different fuel utilizations for a typical type of fuel. The anode exhaust composition can reflect the combined result of the anode reforming reaction, water gas shift reaction, and the anode oxidation reaction. The output composition values in Table 1 were calculated by assuming an anode input composition with an about 2 to 1 ratio of steam ($H_2O$) to carbon (reformable fuel). The reformable fuel was assumed to be methane, which was assumed to be 100% reformed to hydrogen. The initial $CO_2$ and $H_2$ concentrations in the anode input were assumed to be negligible, while the input $N_2$ concentration was about 0.5%. The fuel utilization $U_f$ (as defined herein) was allowed to vary from about 35% to about 70% as shown in the table. The exit temperature for the fuel cell anode was assumed to be about 650° C. for purposes of determining the correct value for the equilibrium constant.

TABLE 1

| Uf | % | 35% | 40% | 45% | 50% | 55% | 60% | 65% | 70% |
|---|---|---|---|---|---|---|---|---|---|
| | | | | Anode Exhaust Composition | | | | | |
| $H_2O$ | %, wet | 32.5% | 34.1% | 35.5% | 36.7% | 37.8% | 38.9% | 39.8% | 40.5% |
| $CO_2$ | %, wet | 26.7% | 29.4% | 32.0% | 34.5% | 36.9% | 39.3% | 41.5% | 43.8% |
| $H_2$ | %, wet | 29.4% | 26.0% | 22.9% | 20.0% | 17.3% | 14.8% | 12.5% | 10.4% |
| CO | %, wet | 10.8% | 10.0% | 9.2% | 8.4% | 7.5% | 6.7% | 5.8% | 4.9% |
| $N_2$ | %, wet | 0.5% | 0.5% | 0.5% | 0.4% | 0.4% | 0.4% | 0.4% | 0.4% |
| $CO_2$ | %, dry | 39.6% | 44.6% | 49.6% | 54.5% | 59.4% | 64.2% | 69.0% | 73.7% |
| $H_2$ | %, dry | 43.6% | 39.4% | 35.4% | 31.5% | 27.8% | 24.2% | 20.7% | 17.5% |
| CO | %, dry | 16.1% | 15.2% | 14.3% | 13.2% | 12.1% | 10.9% | 9.7% | 8.2% |
| $N_2$ | %, dry | 0.7% | 0.7% | 0.7% | 0.7% | 0.7% | 0.7% | 0.7% | 0.7% |
| $H_2/CO$ | | 2.7 | 2.6 | 2.5 | 2.4 | 2.3 | 2.2 | 2.1 | 2.1 |
| $(H_2 - CO_2)/(CO + CO_2)$ | | 0.07 | −0.09 | −0.22 | −0.34 | −0.44 | −0.53 | −0.61 | −0.69 |

Table 1 shows anode output compositions for a particular set of conditions and anode input composition. More generally, in various aspects the anode output can include about 10 vol % to about 50 vol % $H_2O$. The amount of $H_2O$ can vary greatly, as $H_2O$ in the anode can be produced by the anode oxidation reaction. If an excess of $H_2O$ beyond what is needed for reforming is introduced into the anode, the excess $H_2O$ can typically pass through largely unreacted, with the exception of $H_2O$ consumed (or generated) due to fuel reforming and the water gas shift reaction. The $CO_2$ concentration in the anode output can also vary widely, such as from about 20 vol % to about 50 vol % $CO_2$. The amount of $CO_2$ can be influenced by both the amount of electrical current generated as well as the amount of $CO_2$ in the anode input flow. The amount of $H_2$ in the anode output can additionally or alternately be from about 10 vol % $H_2$ to about 50 vol % $H_2$, depending on the fuel utilization in the anode. At the anode output, the amount of CO can be from about 5 vol % to about 20 vol %. It is noted that the amount of CO relative to the amount of $H_2$ in the anode output for a given fuel cell can be determined in part by the equilibrium constant for the water gas shift reaction at the temperature and pressure present in the fuel cell. The anode output can further additionally or alternately include 5 vol % or less of various other components, such as $N_2$, $CH_4$ (or other unreacted carbon-containing fuels), and/or other components.

Optionally, one or more water gas shift reaction stages can be included after the anode output to convert CO and $H_2O$ in the anode output into $CO_2$ and $H_2$, if desired. The amount of $H_2$ present in the anode output can be increased, for example, by using a water gas shift reactor at lower temperature to convert $H_2O$ and CO present in the anode output into $H_2$ and $CO_2$. Alternatively, the temperature can be raised and the water-gas shift reaction can be reversed, producing more CO and $H_2O$ from $H_2$ and $CO_2$. Water is an expected output of the reaction occurring at the anode, so the anode output can typically have an excess of $H_2O$ relative to the amount of CO present in the anode output. Alternatively, $H_2O$ can be added to the stream after the anode exit but before the water gas shift reaction. CO can be present in the anode output due to incomplete carbon conversion during reforming and/or due to the equilibrium balancing reactions between $H_2O$, CO, $H_2$, and $CO_2$ (i.e., the water-gas shift equilibrium) under either reforming conditions or the conditions present during the anode reaction. A water gas shift reactor can be operated under conditions to drive the equilibrium further in the direction of forming $CO_2$ and $H_2$ at the expense of CO and $H_2O$. Higher temperatures can tend to favor the formation of CO and $H_2O$. Thus, one option for operating the water gas shift reactor can be to expose the anode output stream to a suitable catalyst, such as a catalyst including iron oxide, zinc oxide, copper on zinc oxide, or the like, at a suitable temperature, e.g., between about 190° C. to about 210° C. Optionally, the water-gas shift reactor can include two stages for reducing the CO concentration in an anode output stream, with a first higher temperature stage operated at a temperature from at least about 300° C. to about 375° C. and a second lower temperature stage operated at a temperature of about 225° C. or less, such as from about 180° C. to about 210° C. In addition to increasing the amount of $H_2$ present in the anode output, the water-gas shift reaction can additionally or alternately increase the amount of $CO_2$ at the expense of CO. This can exchange difficult-to-remove carbon monoxide (CO) for carbon dioxide, which can be more readily removed by condensation (e.g., cryogenic removal), chemical reaction (such as amine removal), and/or other $CO_2$ removal methods. Additionally or alternately, it may be desirable to increase the CO content present in the anode exhaust in order to achieve a desired ratio of $H_2$ to CO.

After passing through the optional water gas shift reaction stage, the anode output can be passed through one or more separation stages for removal of water and/or $CO_2$ from the anode output stream. For example, one or more $CO_2$ output streams can be formed by performing $CO_2$ separation on the anode output using one or more methods individually or in combination. Such methods can be used to generate $CO_2$ output stream(s) having a $CO_2$ content of 90 vol % or greater, such as at least 95% vol % $CO_2$, or at least 98 vol % $CO_2$. Such methods can recover about at least about 70% of the $CO_2$ content of the anode output, such as at least about 80% of the $CO_2$ content of the anode output, or at least about 90%. Alternatively, in some aspects it may be desirable to recover only a portion of the $CO_2$ within an anode output stream, with the recovered portion of $CO_2$ being about 33% to about 90% of the $CO_2$ in the anode output, such as at least about 40%, or at least about 50%. For example, it may be desirable to retain some $CO_2$ in the anode output flow so that a desired composition can be achieved in a subsequent water gas shift stage. Suitable separation methods may comprise use of a physical solvent (e.g., Selexol™ or Rectisol™); amines or other bases (e.g., MEA or MDEA); refrigeration (e.g., cryogenic separation); pressure swing adsorption; vacuum swing adsorption; and combinations thereof. A cryogenic $CO_2$ separator can be an example of a suitable separator. As the anode output is cooled, the majority of the water in the anode output can be separated out as a condensed (liquid) phase. Further cooling and/or pressurizing of the water-depleted anode output flow can then separate high purity $CO_2$, as the other remaining components in the anode output flow (such as $H_2$, $N_2$, $CH_4$) do not tend to readily form condensed phases. A cryogenic $CO_2$ separator can recover between about 33% and about 90% of the $CO_2$ present in a flow, depending on the operating conditions.

Removal of water from the anode exhaust to form one or more water output streams can also be beneficial, whether prior to, during, or after performing $CO_2$ separation. The amount of water in the anode output can vary depending on operating conditions selected. For example, the steam-to-carbon ratio established at the anode inlet can affect the water content in the anode exhaust, with high steam-to-carbon ratios typically resulting in a large amount of water that can pass through the anode unreacted and/or reacted only due to the water gas shift equilibrium in the anode. Depending on the aspect, the water content in the anode exhaust can correspond to up to about 30% or more of the volume in the anode exhaust. Additionally or alternately, the water content can be about 80% or less of the volume of the anode exhaust. While such water can be removed by compression and/or cooling with resulting condensation, the removal of this water can require extra compressor power and/or heat exchange surface area and excessive cooling water. One beneficial way to remove a portion of this excess water can be based on use of an adsorbent bed that can capture the humidity from the moist anode effluent and can then be 'regenerated' using dry anode feed gas, in order to provide additional water for the anode feed. HVAC-style (heating, ventilation, and air conditioning) adsorption wheels design can be applicable, because anode exhaust and inlet can be similar in pressure, and minor leakage from one stream to the other can have minimal impact on the overall process. In embodiments where $CO_2$ removal is performed using a cryogenic process, removal of water prior to or during $CO_2$ removal may be desirable, including removal by triethyleneglycol (TEG) system and/or desiccants. By contrast, if an amine wash is used for $CO_2$ removal, water can be removed from the anode exhaust downstream from the $CO_2$ removal stage.

Alternately or in addition to a $CO_2$ output stream and/or a water output stream, the anode output can be used to form one or more product streams containing a desired chemical or fuel product. Such a product stream or streams can correspond to a syngas stream, a hydrogen stream, or both syngas product and hydrogen product streams. For example, a hydrogen product stream containing at least about 70 vol % $H_2$, such as at least about 90 vol % $H_2$ or at least about 95 vol % $H_2$, can be formed. Additionally or alternately, a syngas stream containing at least about 70 vol % of $H_2$ and CO combined, such as at least about 90 vol % of $H_2$ and CO can be formed. The one or more product streams can have a gas volume corresponding to at least about 75% of the combined $H_2$ and CO gas volumes in the anode output, such as at least about 85% or at least about 90% of the combined $H_2$ and CO gas volumes. It is noted that the relative amounts of $H_2$ and CO in the products streams may differ from the $H_2$ to CO ratio in the anode output based on use of water gas shift reaction stages to convert between the products.

In some aspects, it can be desirable to remove or separate a portion of the $H_2$ present in the anode output. For example, in some aspects the $H_2$ to CO ratio in the anode exhaust can be at least about 3.0:1. By contrast, processes that make use of syngas, such as Fischer-Tropsch synthesis, may consume $H_2$ and CO in a different ratio, such as a ratio that is closer to 2:1. One alternative can be to use a water gas shift reaction to modify the content of the anode output to have an $H_2$ to CO ratio closer to a desired syngas composition. Another alternative can be to use a membrane separation to remove a portion of the $H_2$ present in the anode output to achieve a desired ratio of $H_2$ and CO, or still alternately to use a combination of membrane separation and water gas shift reactions. One advantage of using a membrane separation to remove only a portion of the $H_2$ in the anode output can be that the desired separation can be performed under relatively mild conditions. Since one goal can be to produce a retentate that still has a substantial $H_2$ content, a permeate of high purity hydrogen can be generated by membrane separation without requiring severe conditions. For example, rather than having a pressure on the permeate side of the membrane of about 100 kPaa or less (such as ambient pressure), the permeate side can be at an elevated pressure relative to ambient while still having sufficient driving force to perform the membrane separation. Additionally or alternately, a sweep gas such as methane can be used to provide a driving force for the membrane separation. This can reduce the purity of the $H_2$ permeate stream, but may be advantageous, depending on the desired use for the permeate stream.

In various aspects of the invention, at least a portion of the anode exhaust stream (preferably after separation of $CO_2$ and/or $H_2O$) can be used as a feed for a process external to the fuel cell and associated reforming stages. In various aspects, the anode exhaust can have a ratio of $H_2$ to CO of about 1.5:1 to about 10:1, such as at least about 3.0:1, or at least about 4.0:1, or at least about 5.0:1. A syngas stream can be generated or withdrawn from the anode exhaust. The anode exhaust gas, optionally after separation of $CO_2$ and/or $H_2O$, and optionally after performing a water gas shift reaction and/or a membrane separation to remove excess hydrogen, can correspond to a stream containing substantial portions of $H_2$ and/or CO. For a stream with a relatively low content of CO, such as a stream where the ratio of $H_2$ to CO is at least about 3:1, the anode exhaust can be suitable for use as an $H_2$ feed. Examples of processes that could benefit from an $H_2$ feed can include, but are not limited to, refinery processes, an ammonia synthesis plant, or a turbine in a (different) power generation system, or combinations thereof. Depending on the application, still lower $CO_2$ contents can be desirable. For a stream with an $H_2$-to-CO ratio of less than about 2.2 to 1 and greater than about 1.9 to 1, the stream can be suitable for use as a syngas feed. Examples of processes that could benefit from a syngas feed can include, but are not limited to, a gas-to-liquids plant (such as a plant using a Fischer-Tropsch process with a non-shifting catalyst) and/or a methanol synthesis plant. The amount of the anode exhaust used as a feed for an external process can be any convenient amount. Optionally, when a portion of the anode exhaust is used as a feed for an external process, a second portion of the anode exhaust can be recycled to the anode input and/or recycled to the combustion zone for a combustion-powered generator.

The input streams useful for different types of Fischer-Tropsch synthesis processes can provide an example of the different types of product streams that may be desirable to generate from the anode output. For a Fischer-Tropsch synthesis reaction system that uses a shifting catalyst, such as an iron-based catalyst, the desired input stream to the reaction system can include $CO_2$ in addition to $H_2$ and CO. If a sufficient amount of $CO_2$ is not present in the input stream, a Fischer-Tropsch catalyst with water gas shift activity can consume CO in order to generate additional $CO_2$, resulting in a syngas that can be deficient in CO. For integration of such a Fischer-Tropsch process with an MCFC fuel cell, the separation stages for the anode output can be operated to retain a desired amount of $CO_2$ (and optionally $H_2O$) in the syngas product. By contrast, for a Fischer-Tropsch catalyst based on a non-shifting catalyst, any $CO_2$ present in a product stream could serve as an inert component in the Fischer-Tropsch reaction system.

In an aspect where the membrane is swept with a sweep gas such as a methane sweep gas, the methane sweep gas can correspond to a methane stream used as the anode fuel or in a different low pressure process, such as a boiler, furnace, gas turbine, or other fuel-consuming device. In such an aspect, low levels of $CO_2$ permeation across the membrane can have minimal consequence. Such $CO_2$ that may permeate across the membrane can have a minimal impact on the reactions within the anode, and such $CO_2$ can remain contained in the anode product. Therefore, the $CO_2$ (if any) lost across the membrane due to permeation does not need to be transferred again across the MCFC electrolyte. This can significantly reduce the separation selectivity requirement for the hydrogen permeation membrane. This can allow, for example, use of a higher-permeability membrane having a lower selectivity, which can enable use of a lower pressure and/or reduced membrane surface area. In such an aspect of the invention, the volume of the sweep gas can be a large multiple of the volume of hydrogen in the anode exhaust, which can allow the effective hydrogen concentration on the permeate side to be maintained close to zero. The hydrogen thus separated can be incorporated into the turbine-fed methane where it can enhance the turbine combustion characteristics, as described above.

It is noted that excess $H_2$ produced in the anode can represent a fuel where the greenhouse gases have already been separated. Any $CO_2$ in the anode output can be readily separated from the anode output, such as by using an amine wash, a cryogenic $CO_2$ separator, and/or a pressure or vacuum swing absorption process. Several of the components of the anode output ($H_2$, CO, $CH_4$) are not easily removed, while $CO_2$ and $H_2O$ can usually be readily removed. Depending on the embodiment, at least about 90 vol % of the $CO_2$ in the anode output can be separated out to form a relatively high purity $CO_2$ output stream. Thus, any $CO_2$ generated in the anode can be efficiently separated out to form a high purity $CO_2$ output stream. After separation, the remaining portion of the anode output can correspond primarily to components with chemical and/or fuel value, as well as reduced amounts of $CO_2$ and/or $H_2O$. Since a substantial portion of the $CO_2$ generated by the original fuel (prior to reforming) can have been separated out, the amount of $CO_2$ generated by subsequent burning of the remaining portion of the anode output can be reduced. In particular, to the degree that the fuel in the remaining portion of the anode output is $H_2$, no additional greenhouse gases can typically be formed by burning of this fuel.

The anode exhaust can be subjected to a variety of gas processing options, including water-gas shift and separation of the components from each other. Two general anode processing schemes are shown in FIGS. 1 and 2.

Figure 2:
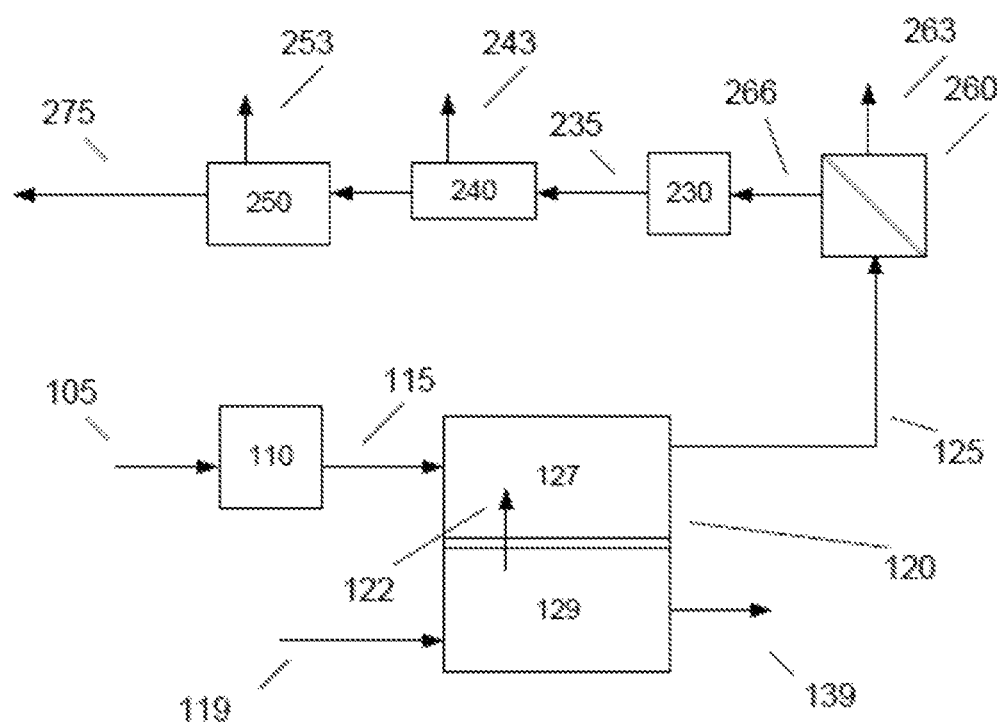
FIG. 2 schematically shows another example of a configuration for molten carbonate fuel cells and associated reforming and separation stages.

FIG. 1 schematically shows an example of a reaction system for operating a fuel cell array of molten carbonate fuel cells in conjunction with a chemical synthesis process. In FIG. 1, a fuel stream 105 is provided to a reforming stage (or stages) 110 associated with the anode 127 of a fuel cell 120, such as a fuel cell that is part of a fuel cell stack in a fuel cell array. The reforming stage 110 associated with fuel cell 120 can be internal to a fuel cell assembly. In some optional aspects, an external reforming stage (not shown) can also be used to reform a portion of the reformable fuel in an input stream prior to passing the input stream into a fuel cell assembly. Fuel stream 105 can preferably include a reformable fuel, such as methane, other hydrocarbons, and/or other hydrocarbon-like compounds such as organic compounds containing carbon-hydrogen bonds. Fuel stream 105 can also optionally contain $H_2$ and/or CO, such as $H_2$ and/or CO provided by optional anode recycle stream 185. It is noted that anode recycle stream 185 is optional, and that in many aspects no recycle stream is provided from the anode exhaust 125 back to anode 127, either directly or indirectly via combination with fuel stream 105 or reformed fuel stream 115. After reforming, the reformed fuel stream 115 can be passed into anode 127 of fuel cell 120. A $CO_2$ and $O_2$-containing stream 119 can also be passed into cathode 129. A flow of carbonate ions 122, $CO_3^{2-}$, from the cathode portion 129 of the fuel cell can provide the remaining reactant needed for the anode fuel cell reactions. Based on the reactions in the anode 127, the resulting anode exhaust 125 can include $H_2O$, $CO_2$, one or more components corresponding to incompletely reacted fuel ($H_2$, CO, $CH_4$, or other components corresponding to a reformable fuel), and optionally one or more additional nonreactive components, such as $N_2$ and/or other contaminants that are part of fuel stream 105. The anode exhaust 125 can then be passed into one or more separation stages. For example, a $CO_2$ removal stage 140 can correspond to a cryogenic $CO_2$ removal system, an amine wash stage for removal of acid gases such as $CO_2$, or another suitable type of $CO_2$ separation stage for separating a $CO_2$ output stream 143 from the anode exhaust. Optionally, the anode exhaust can first be passed through a water gas shift reactor 130 to convert any CO present in the anode exhaust (along with some $H_2O$) into $CO_2$ and $H_2$ in an optionally water gas shifted anode exhaust 135. Depending on the nature of the $CO_2$ removal stage, a water condensation or removal stage 150 may be desirable to remove a water output stream 153 from the anode exhaust. Though shown in FIG. 1 after the $CO_2$ separation stage 140, it may optionally be located before the $CO_2$ separation stage 140 instead. Additionally, an optional membrane separation stage 160 for separation of $H_2$ can be used to generate a high purity permeate stream 163 of $H_2$. The resulting retentate stream 166 can then be used as an input to a chemical synthesis process. Stream 166 could additionally or alternately be shifted in a second water-gas shift reactor 131 to adjust the $H_2$, CO, and $CO_2$ content to a different ratio, producing an output stream 168 for further use in a chemical synthesis process. In FIG. 1, anode recycle stream 185 is shown as being withdrawn from the retentate stream 166, but the anode recycle stream 185 could additionally or alternately be withdrawn from other convenient locations in or between the various separation stages. The separation stages and shift reactor(s) could additionally or alternately be configured in different orders, and/or in a parallel configuration. Finally, a stream with a reduced content of $CO_2$ 139 can be generated as an output from cathode 129. For the sake of simplicity, various stages of compression and heat addition/removal that might be useful in the process, as well as steam addition or removal, are not shown.

As noted above, the various types of separations performed on the anode exhaust can be performed in any convenient order. FIG. 2 shows an example of an alternative order for performing separations on an anode exhaust. In FIG. 2, anode exhaust 125 can be initially passed into separation stage 260 for removing a portion 263 of the hydrogen content from the anode exhaust 125. This can allow, for example, reduction of the $H_2$ content of the anode exhaust to provide a retentate 266 with a ratio of $H_2$ to CO closer to 2:1. The ratio of $H_2$ to CO can then be further adjusted to achieve a desired value in a water gas shift stage 230. The water gas shifted output 235 can then pass through $CO_2$ separation stage 240 and water removal stage 250 to produce an output stream 275 suitable for use as an input to a desired chemical synthesis process. Optionally, output stream 275 could be exposed to an additional water gas shift stage (not shown). A portion of output stream 275 can optionally be recycled (not shown) to the anode input. Of course, still other combinations and sequencing of separation stages can be used to generate a stream based on the anode output that has a desired composition. For the sake of simplicity, various stages of compression and heat addition/removal that might be useful in the process, as well as steam addition or removal, are not shown.

Cathode Inputs and Outputs

Conventionally, a molten carbonate fuel cell can be operated based on drawing a desired load while consuming some portion of the fuel in the fuel stream delivered to the anode. The voltage of the fuel cell can then be determined by the load, fuel input to the anode, air and $CO_2$ provided to the cathode, and the internal resistances of the fuel cell. The $CO_2$ to the cathode can be conventionally provided in part by using the anode exhaust as at least a part of the cathode input stream. By contrast, the present invention can use separate/different sources for the anode input and cathode input. By removing any direct link between the composition of the anode input flow and the cathode input flow, additional options become available for operating the fuel cell, such as to generate excess synthesis gas, to improve capture of carbon dioxide, and/or to improve the total efficiency (electrical plus chemical power) of the fuel cell, among others.

In a molten carbonate fuel cell, the transport of carbonate ions across the electrolyte in the fuel cell can provide a method for transporting $CO_2$ from a first flow path to a second flow path, where the transport method can allow transport from a lower concentration (the cathode) to a higher concentration (the anode), which can thus facilitate capture of $CO_2$. Part of the selectivity of the fuel cell for $CO_2$ separation can be based on the electrochemical reactions allowing the cell to generate electrical power. For nonreactive species (such as $N_2$) that effectively do not participate in the electrochemical reactions within the fuel cell, there can be an insignificant amount of reaction and transport from cathode to anode. By contrast, the potential (voltage) difference between the cathode and anode can provide a strong driving force for transport of carbonate ions across the fuel cell. As a result, the transport of carbonate ions in the molten carbonate fuel cell can allow $CO_2$ to be transported from the cathode (lower $CO_2$ concentration) to the anode (higher $CO_2$ concentration) with relatively high selectivity. However, a challenge in using molten carbonate fuel cells for carbon dioxide removal can be that the fuel cells have limited ability to remove carbon dioxide from relatively dilute cathode feeds. The voltage and/or power generated by a carbonate fuel cell can start to drop rapidly as the $CO_2$ concentration falls below about 2.0 vol %. As the $CO_2$ concentration drops further, e.g., to below about 1.0 vol %, at some point the voltage across the fuel cell can become low enough that little or no further transport of carbonate may occur and the fuel cell ceases to function. Thus, at least some $CO_2$ is likely to be present in the exhaust gas from the cathode stage of a fuel cell under commercially viable operating conditions.

The amount of carbon dioxide delivered to the fuel cell cathode(s) can be determined based on the $CO_2$ content of a source for the cathode inlet. One example of a suitable $CO_2$-containing stream for use as a cathode input flow can be an output or exhaust flow from a combustion source. Examples of combustion sources include, but are not limited to, sources based on combustion of natural gas, combustion of coal, and/or combustion of other hydrocarbon-type fuels (including biologically derived fuels). Additional or alternate sources can include other types of boilers, fired heaters, furnaces, and/or other types of devices that burn carbon-containing fuels in order to heat another substance (such as water or air). To a first approximation, the $CO_2$ content of the output flow from a combustion source can be a minor portion of the flow. Even for a higher $CO_2$ content exhaust flow, such as the output from a coal-fired combustion source, the $CO_2$ content from most commercial coal-fired power plants can be about 15 vol % or less. More generally, the $CO_2$ content of an output or exhaust flow from a combustion source can be at least about 1.5 vol %, or at least about 1.6 vol %, or at least about 1.7 vol %, or at least about 1.8 vol %, or at least about 1.9 vol %, or at least greater 2 vol %, or at least about 4 vol %, or at least about 5 vol %, or at least about 6 vol %, or at least about 8 vol %. Additionally or alternately, the $CO_2$ content of an output or exhaust flow from a combustion source can be about 20 vol % or less, such as about 15 vol % or less, or about 12 vol % or less, or about 10 vol % or less, or about 9 vol % or less, or about 8 vol % or less, or about 7 vol % or less, or about 6.5 vol % or less, or about 6 vol % or less, or about 5.5 vol % or less, or about 5 vol % or less, or about 4.5 vol % or less. The concentrations given above are on a dry basis. It is noted that the lower $CO_2$ content values can be present in the exhaust from some natural gas or methane combustion sources, such as generators that are part of a power generation system that may or may not include an exhaust gas recycle loop.

Other potential sources for a cathode input stream can additionally or alternately include sources of bio-produced $CO_2$. This can include, for example, $CO_2$ generated during processing of bio-derived compounds, such as $CO_2$ generated during ethanol production. An additional or alternate example can include $CO_2$ generated by combustion of a bio-produced fuel, such as combustion of lignocellulose. Still other additional or alternate potential $CO_2$ sources can correspond to output or exhaust streams from various industrial processes, such as $CO_2$-containing streams generated by plants for manufacture of steel, cement, and/or paper.

Yet another additional or alternate potential source of $CO_2$ can be $CO_2$-containing streams from a fuel cell. The $CO_2$-containing stream from a fuel cell can correspond to a cathode output stream from a different fuel cell, an anode output stream from a different fuel cell, a recycle stream from the cathode output to the cathode input of a fuel cell, and/or a recycle stream from an anode output to a cathode input of a fuel cell. For example, an MCFC operated in standalone mode under conventional conditions can generate a cathode exhaust with a $CO_2$ concentration of at least about 5 vol %. Such a $CO_2$-containing cathode exhaust could be used as a cathode input for an MCFC operated according to an aspect of the invention. More generally, other types of fuel cells that generate a $CO_2$ output from the cathode exhaust can additionally or alternatively be used, as well as other types of $CO_2$-containing streams not generated by a "combustion" reaction and/or by a combustion-powered generator. Optionally but preferably, a $CO_2$-containing stream from another fuel cell can be from another molten carbonate fuel cell. For example, for molten carbonate fuel cells connected in series with respect to the cathodes, the output from the cathode for a first molten carbonate fuel cell can be used as the input to the cathode for a second molten carbonate fuel cell.

For various types of $CO_2$-containing streams from sources other than combustion sources, the $CO_2$ content of the stream can vary widely. The $CO_2$ content of an input stream to a cathode can contain at least about 2 vol % of $CO_2$, such as at least about 4 vol %, or at least about 5 vol %, or at least about 6 vol %, or at least about 8 vol %. Additionally or alternatively, the $CO_2$ content of an input stream to a cathode can be about 30 vol % or less, such as about 25 vol % or less, or about 20 vol % or less, or about 15 vol % or less, or about 10 vol % or less, or about 8 vol % or less, or about 6 vol % or less, or about 4 vol % or less. For some still higher $CO_2$ content streams, the $CO_2$ content can be greater than about 30 vol %, such as a stream substantially composed of $CO_2$ with only incidental amounts of other compounds. As an example, a gas-fired turbine without exhaust gas recycle can produce an exhaust stream with a $CO_2$ content of approximately 4.2 vol %. With EGR, a gas-fired turbine can produce an exhaust stream with a $CO_2$ content of about 6-8 vol %. Stoichiometric combustion of methane can produce an exhaust stream with a $CO_2$ content of about 11 vol %. Combustion of coal can produce an exhaust stream with a $CO_2$ content of about 15-20 vol %. Fired heaters using refinery off-gas can produce an exhaust stream with a $CO_2$ content of about 12-15 vol %. A gas turbine operated on a low BTU gas without any EGR can produce an exhaust stream with a $CO_2$ content of ~12 vol %.

In addition to $CO_2$, a cathode input stream must include $O_2$ to provide the components necessary for the cathode reaction. Some cathode input streams can be based on having air as a component. For example, a combustion exhaust stream can be formed by combusting a hydrocarbon fuel in the presence of air. Such a combustion exhaust stream, or another type of cathode input stream having an oxygen content based on inclusion of air, can have an oxygen content of about 20 vol % or less, such as about 15 vol % or less, or about 10 vol % or less. Additionally or alternatively, the oxygen content of the cathode input stream can be at least about 4 vol %, such as at least about 6 vol %, or at least about 8 vol %. More generally, a cathode input stream can have a suitable content of oxygen for performing the cathode reaction. In some aspects, this can correspond to an oxygen content of about 5 vol % to about 15 vol %, such as from about 7 vol % to about 9 vol %. For many types of cathode input streams, the combined amount of $CO_2$ and $O_2$ can correspond to less than about 21 vol % of the input stream, such as less than about 15 vol % of the stream or less than about 10 vol % of the stream. An air stream containing oxygen can be combined with a $CO_2$ source that has low oxygen content. For example, the exhaust stream generated by burning coal may include a low oxygen content that can be mixed with air to form a cathode inlet stream.

In addition to $CO_2$ and $O_2$, a cathode input stream can also be composed of inert/non-reactive species such as $N_2$, $H_2O$, and other typical oxidant (air) components. For example, for a cathode input derived from an exhaust from a combustion reaction, if air is used as part of the oxidant source for the combustion reaction, the exhaust gas can include typical components of air such as $N_2$, $H_2O$, and other compounds in minor amounts that are present in air. Depending on the nature of the fuel source for the combustion reaction, additional species present after combustion based on the fuel source may include one or more of $H_2O$, oxides of nitrogen (NOx) and/or sulfur (SOx), and other compounds either present in the fuel and/or that are partial or complete combustion products of compounds present in the fuel, such as CO. These species may be present in amounts that do not poison the cathode catalyst surfaces though they may reduce the overall cathode activity. Such reductions in performance may be acceptable, or species that interact with the cathode catalyst may be reduced to acceptable levels by known pollutant removal technologies.

The amount of $O_2$ present in a cathode input stream (such as an input cathode stream based on a combustion exhaust) can advantageously be sufficient to provide the oxygen needed for the cathode reaction in the fuel cell. Thus, the volume percentage of $O_2$ can advantageously be at least 0.5 times the amount of $CO_2$ in the exhaust. Optionally, as necessary, additional air can be added to the cathode input to provide sufficient oxidant for the cathode reaction. When some form of air is used as the oxidant, the amount of $N_2$ in the cathode exhaust can be at least about 78 vol %, e.g., at least about 88 vol %, and/or about 95 vol % or less. In some aspects, the cathode input stream can additionally or alternately contain compounds that are generally viewed as contaminants, such as $H_2S$ or $NH_3$. In other aspects, the cathode input stream can be cleaned to reduce or minimize the content of such contaminants.

In addition to the reaction to form carbonate ions for transport across the electrolyte, the conditions in the cathode can also be suitable for conversion of nitrogen oxides into nitrate and/or nitrate ions. Hereinafter, only nitrate ions will be referred to for convenience. The resulting nitrate ions can also be transported across the electrolyte for reaction in the anode. NOx concentrations in a cathode input stream can typically be on the order of ppm, so this nitrate transport reaction can have a minimal impact on the amount of carbonate transported across the electrolyte. However, this method of NOx removal can be beneficial for cathode input streams based on combustion exhausts from gas turbines, as this can provide a mechanism for reducing NOx emissions. The conditions in the cathode can additionally or alternately be suitable for conversion of unburned hydrocarbons (in combination with $O_2$ in the cathode input stream) to typical combustion products, such as $CO_2$ and $H_2O$.

A suitable temperature for operation of an MCFC can be between about 450° C. and about 750° C., such as at least about 500° C., e.g., with an inlet temperature of about 550° C. and an outlet temperature of about 625° C. Prior to entering the cathode, heat can be added to or removed from the combustion exhaust, if desired, e.g., to provide heat for other processes, such as reforming the fuel input for the anode. For example, if the source for the cathode input stream is a combustion exhaust stream, the combustion exhaust stream may have a temperature greater than a desired temperature for the cathode inlet. In such an aspect, heat can be removed from the combustion exhaust prior to use as the cathode input stream. Alternatively, the combustion exhaust could be at very low temperature, for example after a wet gas scrubber on a coal-fired boiler, in which case the combustion exhaust can be below about 100° C. Alternatively, the combustion exhaust could be from the exhaust of a gas turbine operated in combined cycle mode, in which the gas can be cooled by raising steam to run a steam turbine for additional power generation. In this case, the gas can be below about 50° C. Heat can be added to a combustion exhaust that is cooler than desired.

Fuel Cell Arrangement

In various aspects, a configuration option for a fuel cell (such as a fuel cell array containing multiple fuel cell stacks) can be to divide the $CO_2$-containing stream between a plurality of fuel cells. Some types of sources for $CO_2$- containing streams can generate large volumetric flow rates relative to the capacity of an individual fuel cell. For example, the $CO_2$-containing output stream from an industrial combustion source can typically correspond to a large flow volume relative to desirable operating conditions for a single MCFC of reasonable size. Instead of processing the entire flow in a single MCFC, the flow can be divided amongst a plurality of MCFC units, usually at least some of which can be in parallel, so that the flow rate in each unit can be within a desired flow range.

A second configuration option can be to utilize fuel cells in series to successively remove $CO_2$ from a flow stream. Regardless of the number of initial fuel cells to which a $CO_2$-containing stream can be distributed to in parallel, each initial fuel cell can be followed by one or more additional cells in series to further remove additional $CO_2$. If the desired amount of $CO_2$ in the cathode output is sufficiently low, attempting to remove $CO_2$ from a cathode input stream down to the desired level in a single fuel cell or fuel cell stage could lead to a low and/or unpredictable voltage output for the fuel cell. Rather than attempting to remove $CO_2$ to the desired level in a single fuel cell or fuel cell stage, $CO_2$ can be removed in successive cells until a desired level can be achieved. For example, each cell in a series of fuel cells can be used to remove some percentage (e.g., about 50%) of the $CO_2$ present in a fuel stream. In such an example, if three fuel cells are used in series, the $CO_2$ concentration can be reduced (e.g., to about 15% or less of the original amount present, which can correspond to reducing the $CO_2$ concentration from about 6% to about 1% or less over the course of three fuel cells in series).

In another configuration, the operating conditions can be selected in early fuel stages in series to provide a desired output voltage while the array of stages can be selected to achieve a desired level of carbon separation. As an example, an array of fuel cells can be used with three fuel cells in series. The first two fuel cells in series can be used to remove $CO_2$ while maintaining a desired output voltage. The final fuel cell can then be operated to remove $CO_2$ to a desired concentration but at a lower voltage.

In still another configuration, there can be separate connectivity for the anodes and cathodes in a fuel cell array. For example, if the fuel cell array includes fuel cathodes connected in series, the corresponding anodes can be connected in any convenient manner, not necessarily matching up with the same arrangement as their corresponding cathodes, for example. This can include, for instance, connecting the anodes in parallel, so that each anode receives the same type of fuel feed, and/or connecting the anodes in a reverse series, so that the highest fuel concentration in the anodes can correspond to those cathodes having the lowest $CO_2$ concentration.

In yet another configuration, the amount of fuel delivered to one or more anode stages and/or the amount of $CO_2$ delivered to one or more cathode stages can be controlled in order to improve the performance of the fuel cell array. For example, a fuel cell array can have a plurality of cathode stages connected in series. In an array that includes three cathode stages in series, this can mean that the output from a first cathode stage can correspond to the input for a second cathode stage, and the output from the second cathode stage can correspond to the input for a third cathode stage. In this type of configuration, the $CO_2$ concentration can decrease with each successive cathode stage. To compensate for this reduced $CO_2$ concentration, additional hydrogen and/or methane can be delivered to the anode stages corresponding to the later cathode stages. The additional hydrogen and/or methane in the anodes corresponding to the later cathode stages can at least partially offset the loss of voltage and/or current caused by the reduced $CO_2$ concentration, which can increase the voltage and thus net power produced by the fuel cell. In another example, the cathodes in a fuel cell array can be connected partially in series and partially in parallel. In this type of example, instead of passing the entire combustion output into the cathodes in the first cathode stage, at least a portion of the combustion exhaust can be passed into a later cathode stage. This can provide an increased $CO_2$ content in a later cathode stage. Still other options for using variable feeds to either anode stages or cathode stages can be used if desired.

The cathode of a fuel cell can correspond to a plurality of cathodes from an array of fuel cells, as previously described. In some aspects, a fuel cell array can be operated to improve or maximize the amount of carbon transferred from the cathode to the anode. In such aspects, for the cathode output from the final cathode(s) in an array sequence (typically at least including a series arrangement, or else the final cathode(s) and the initial cathode(s) would be the same), the output composition can include about 2.0 vol % or less of $CO_2$ (e.g., about 1.5 vol % or less or about 1.2 vol % or less) and/or at least about 0.5 vol % of $CO_2$, or at least about 1.0 vol %, or at least about 1.2 vol % or at least about 1.5 vol %. Due to this limitation, the net efficiency of $CO_2$ removal when using molten carbonate fuel cells can be dependent on the amount of $CO_2$ in the cathode input. For cathode input streams with $CO_2$ contents of greater than about 6 vol %, such as at least about 8%, the limitation on the amount of $CO_2$ that can be removed is not severe. However, for a combustion reaction using natural gas as a fuel and with excess air, as is typically found in a gas turbine, the amount of $CO_2$ in the combustion exhaust may only correspond to a $CO_2$ concentration at the cathode input of less than about 5 vol %. Use of exhaust gas recycle can allow the amount of $CO_2$ at the cathode input to be increased to at least about 5 vol %, e.g., at least about 6 vol %. If EGR is increased when using natural gas as a fuel to produce a $CO_2$ concentration beyond about 6 vol %, then the flammability in the combustor can be decreased and the gas turbine may become unstable. However, when $H_2$ is added to the fuel, the flammability window can be significantly increased, allowing the amount of exhaust gas recycle to be increased further, so that concentrations of $CO_2$ at the cathode input of at least about 7.5 vol % or at least about 8 vol % can be achieved. As an example, based on a removal limit of about 1.5 vol % at the cathode exhaust, increasing the $CO_2$ content at the cathode input from about 5.5 vol % to about 7.5 vol % can correspond to a ~10% increase in the amount of $CO_2$ that can be captured using a fuel cell and transported to the anode loop for eventual $CO_2$ separation. The amount of $O_2$ in the cathode output can additionally or alternately be reduced, typically in an amount proportional to the amount of $CO_2$ removed, which can result in small corresponding increases in the amount(s) of the other (non-cathode-reactive) species at the cathode exit.

In other aspects, a fuel cell array can be operated to improve or maximize the energy output of the fuel cell, such as the total energy output, the electric energy output, the syngas chemical energy output, or a combination thereof. For example, molten carbonate fuel cells can be operated with an excess of reformable fuel in a variety of situations, such as for generation of a syngas stream for use in chemical synthesis plant and/or for generation of a high purity hydrogen stream. The syngas stream and/or hydrogen stream can be used as a syngas source, a hydrogen source, as a clean fuel source, and/or for any other convenient application. In such aspects, the amount of $CO_2$ in the cathode exhaust can be related to the amount of $CO_2$ in the cathode input stream and the $CO_2$ utilization at the desired operating conditions for improving or maximizing the fuel cell energy output.

Additionally or alternately, depending on the operating conditions, an MCFC can lower the $CO_2$ content of a cathode exhaust stream to about 5.0 vol % or less, e.g., about 4.0 vol % or less, or about 2.0 vol % or less, or about 1.5 vol % or less, or about 1.2 vol % or less. Additionally or alternately, the $CO_2$ content of the cathode exhaust stream can be at least about 0.9 vol %, such as at least about 1.0 vol %, or at least about 1.2 vol %, or at least about 1.5 vol %.

Molten Carbonate Fuel Cell Operation

In some aspects, a fuel cell may be operated in a single pass or once-through mode. In single pass mode, reformed products in the anode exhaust are not returned to the anode inlet. Thus, recycling syngas, hydrogen, or some other product from the anode output directly to the anode inlet is not done in single pass operation. More generally, in single pass operation, reformed products in the anode exhaust are also not returned indirectly to the anode inlet, such as by using reformed products to process a fuel stream subsequently introduced into the anode inlet. Optionally, $CO_2$ from the anode outlet can be recycled to the cathode inlet during operation of an MCFC in single pass mode. More generally, in some alternative aspects, recycling from the anode outlet to the cathode inlet may occur for an MCFC operating in single pass mode. Heat from the anode exhaust or output may additionally or alternately be recycled in a single pass mode. For example, the anode output flow may pass through a heat exchanger that cools the anode output and warms another stream, such as an input stream for the anode and/or the cathode. Recycling heat from anode to the fuel cell is consistent with use in single pass or once-through operation. Optionally but not preferably, constituents of the anode output may be burned to provide heat to the fuel cell during single pass mode.

Figure 3:
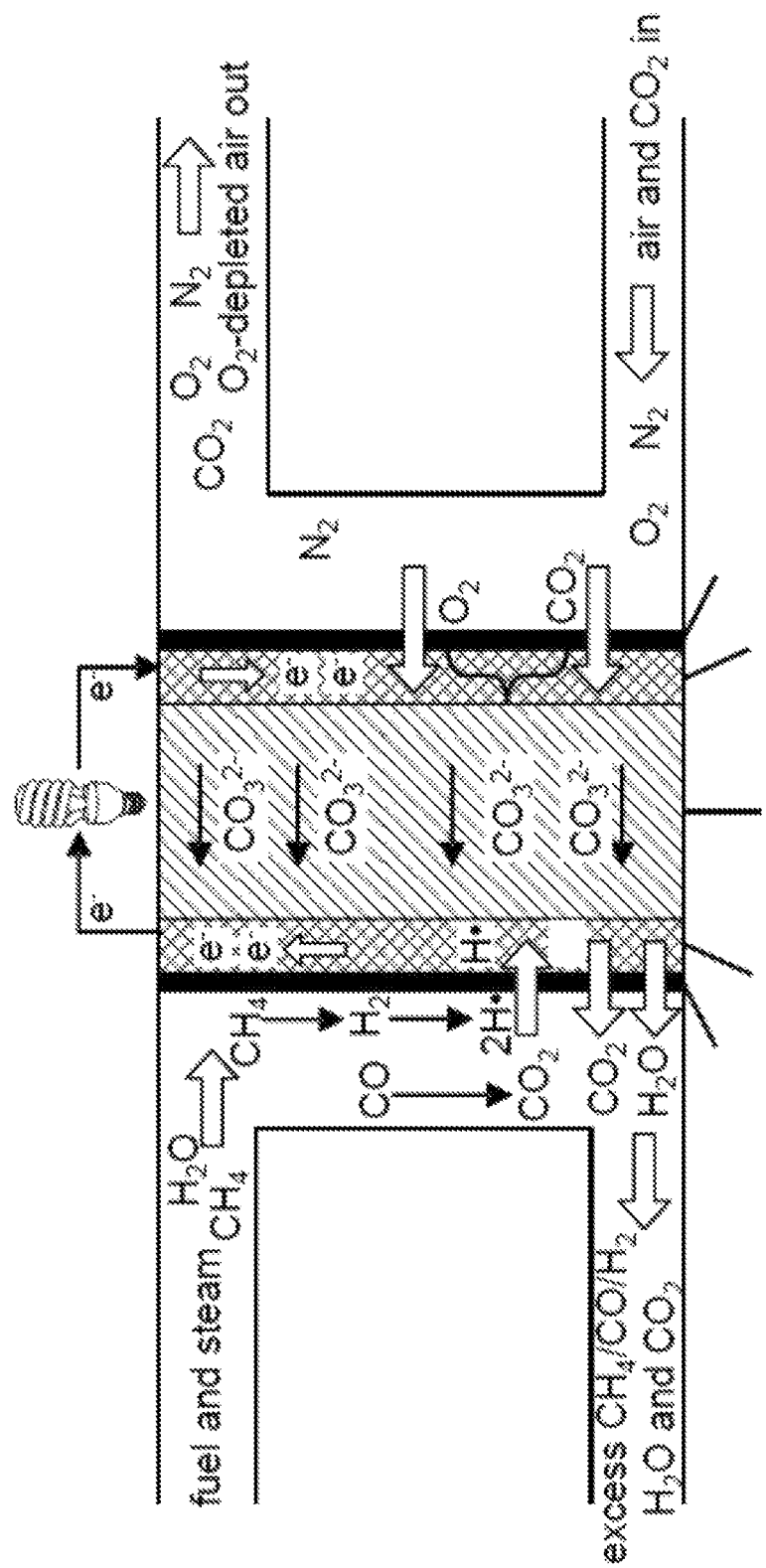
FIG. 3 schematically shows an example of the operation of a molten carbonate fuel cell.

FIG. 3 shows a schematic example of the operation of an MCFC for generation of electrical power. In FIG. 3, the anode portion of the fuel cell can receive fuel and steam ($H_2O$) as inputs, with outputs of water, $CO_2$, and optionally excess $H_2$, $CH_4$ (or other hydrocarbons), and/or CO. The cathode portion of the fuel cell can receive $CO_2$ and some oxidant (e.g., air/$O_2$) as inputs, with an output corresponding to a reduced amount of $CO_2$ in $O_2$-depleted oxidant (air). Within the fuel cell, $CO_3^{2-}$ ions formed in the cathode side can be transported across the electrolyte to provide the carbonate ions needed for the reactions occurring at the anode.

Several reactions can occur within a molten carbonate fuel cell such as the example fuel cell shown in FIG. 3. The reforming reactions can be optional, and can be reduced or eliminated if sufficient $H_2$ is provided directly to the anode. The following reactions are based on $CH_4$, but similar reactions can occur when other fuels are used in the fuel cell.

(1) <anode reforming> $CH_4 + H_2O \Rightarrow 3H_2 + CO$
(2) <water gas shift> $CO + H_2O \Rightarrow H_2 + CO_2$
(3) <reforming and water gas shift combined> $CH_4 + 2H_2O \Rightarrow 4H_2 + CO_2$
(4) <anode $H_2$ oxidation> $H_2 + CO_3^{2-} \Rightarrow H_2O + CO_2 + 2e^-$
(5) <cathode> $\frac{1}{2}O_2 + CO_2 + 2e^- \Rightarrow CO_3^{2-}$ Reaction (1) represents the basic hydrocarbon reforming reaction to generate $H_2$ for use in the anode of the fuel cell. The CO formed in reaction (1) can be converted to $H_2$ by the water-gas shift reaction (2). The combination of reactions (1) and (2) is shown as reaction (3). Reactions (1) and (2) can occur external to the fuel cell, and/or the reforming can be performed internal to the anode.

Reactions (4) and (5), at the anode and cathode respectively, represent the reactions that can result in electrical power generation within the fuel cell. Reaction (4) combines $H_2$, either present in the feed or optionally generated by reactions (1) and/or (2), with carbonate ions to form $H_2O$, $CO_2$, and electrons to the circuit. Reaction (5) combines $O_2$, $CO_2$, and electrons from the circuit to form carbonate ions. The carbonate ions generated by reaction (5) can be transported across the electrolyte of the fuel cell to provide the carbonate ions needed for reaction (4). In combination with the transport of carbonate ions across the electrolyte, a closed current loop can then be formed by providing an electrical connection between the anode and cathode.

In various embodiments, a goal of operating the fuel cell can be to improve the total efficiency of the fuel cell and/or the total efficiency of the fuel cell plus an integrated chemical synthesis process. This is typically in contrast to conventional operation of a fuel cell, where the goal can be to operate the fuel cell with high electrical efficiency for using the fuel provided to the cell for generation of electrical power. As defined above, total fuel cell efficiency may be determined by dividing the electric output of the fuel cell plus the lower heating value of the fuel cell outputs by the lower heating value of the input components for the fuel cell. In other words, TFCE=(LHV(el)+LHV(sg out))/LHV(in), where LHV(in) and LHV(sg out) refer to the LHV of the fuel components (such as $H_2$, $CH_4$, and/or CO) delivered to the fuel cell and syngas ($H_2$, CO and/or $CO_2$) in the anode outlet streams or flows, respectively. This can provide a measure of the electric energy plus chemical energy generated by the fuel cell and/or the integrated chemical process. It is noted that under this definition of total efficiency, heat energy used within the fuel cell and/or used within the integrated fuel cell/chemical synthesis system can contribute to total efficiency. However, any excess heat exchanged or otherwise withdrawn from the fuel cell or integrated fuel cell/chemical synthesis system is excluded from the definition. Thus, if excess heat from the fuel cell is used, for example, to generate steam for electricity generation by a steam turbine, such excess heat is excluded from the definition of total efficiency.

Several operational parameters may be manipulated to operate a fuel cell with excess reformable fuel. Some parameters can be similar to those currently recommended for fuel cell operation. In some aspects, the cathode conditions and temperature inputs to the fuel cell can be similar to those recommended in the literature. For example, the desired electrical efficiency and the desired total fuel cell efficiency may be achieved at a range of fuel cell operating temperatures typical for molten carbonate fuel cells. In typical operation, the temperature can increase across the fuel cell.

In other aspects, the operational parameters of the fuel cell can deviate from typical conditions so that the fuel cell is operated to allow a temperature decrease from the anode inlet to the anode outlet and/or from the cathode inlet to the cathode outlet. For example, the reforming reaction to convert a hydrocarbon into $H_2$ and CO is an endothermic reaction. If a sufficient amount of reforming is performed in a fuel cell anode relative to the amount of oxidation of hydrogen to generate electrical current, the net heat balance in the fuel cell can be endothermic. This can cause a temperature drop between the inlets and outlets of a fuel cell. During endothermic operation, the temperature drop in the fuel cell can be controlled so that the electrolyte in the fuel cell remains in a molten state.

Parameters that can be manipulated in a way so as to differ from those currently recommended can include the amount of fuel provided to the anode, the composition of the fuel provided to the anode, and/or the separation and capture of syngas in the anode output without significant recycling of syngas from the anode exhaust to either the anode input or the cathode input. In some aspects, no recycle of syngas or hydrogen from the anode exhaust to either the anode input or the cathode input can be allowed to occur, either directly or indirectly. In additional or alternative aspects, a limited amount of recycle can occur. In such aspects, the amount of recycle from the anode exhaust to the anode input and/or the cathode input can be less than about 10 vol % of the anode exhaust, such as less than about 5 vol %, or less than about 1 vol %.

Additionally or alternately, a goal of operating a fuel cell can be to separate $CO_2$ from the output stream of a combustion reaction or another process that produces a $CO_2$ output stream, in addition to allowing generation of electric power. In such aspects, the combustion reaction(s) can be used to power one or more generators or turbines, which can provide a majority of the power generated by the combined generator/fuel cell system. Rather than operating the fuel cell to optimize power generation by the fuel cell, the system can instead be operated to improve the capture of carbon dioxide from the combustion-powered generator while reducing or minimizing the number of fuels cells required for capturing the carbon dioxide. Selecting an appropriate configuration for the input and output flows of the fuel cell, as well as selecting appropriate operating conditions for the fuel cell, can allow for a desirable combination of total efficiency and carbon capture.

In some embodiments, the fuel cells in a fuel cell array can be arranged so that only a single stage of fuel cells (such as fuel cell stacks) can be present. In this type of embodiment, the anode fuel utilization for the single stage can represent the anode fuel utilization for the array. Another option can be that a fuel cell array can contain multiple stages of anodes and multiple stages of cathodes, with each anode stage having a fuel utilization within the same range, such as each anode stage having a fuel utilization within 10% of a specified value, for example within 5% of a specified value. Still another option can be that each anode stage can have a fuel utilization equal to a specified value or lower than the specified value by less than an amount, such as having each anode stage be not greater than a specified value by 10% or less, for example, by 5% or less. As an illustrative example, a fuel cell array with a plurality of anode stages can have each anode stage be within about 10% of 50% fuel utilization, which would correspond to each anode stage having a fuel utilization between about 40% and about 60%. As another example, a fuel cell array with a plurality of stages can have each anode stage be not greater than 60% anode fuel utilization with the maximum deviation being about 5% less, which would correspond to each anode stage having a fuel utilization between about 55% to about 60%. In still another example, one or more stages of fuel cells in a fuel cell array can be operated at a fuel utilization from about 30% to about 50%, such as operating a plurality of fuel cell stages in the array at a fuel utilization from about 30% to about 50%. More generally, any of the above types of ranges can be paired with any of the anode fuel utilization values specified herein.

Still another additional or alternate option can include specifying a fuel utilization for less than all of the anode stages. For example, in some aspects of the invention fuel cells/stacks can be arranged at least partially in one or more series arrangements such that anode fuel utilization can be specified for the first anode stage in a series, the second anode stage in a series, the final anode stage in a series, or any other convenient anode stage in a series. As used herein, the "first" stage in a series corresponds to the stage (or set of stages, if the arrangement contains parallel stages as well) to which input is directly fed from the fuel source(s), with later ("second," "third," "final," etc.) stages representing the stages to which the output from one or more previous stages is fed, instead of directly from the respective fuel source(s). In situations where both output from previous stages and input directly from the fuel source(s) are co-fed into a stage, there can be a "first" (set of) stage(s) and a "last" (set of) stage(s), but other stages ("second," "third," etc.) can be more tricky among which to establish an order (e.g., in such cases, ordinal order can be determined by concentration levels of one or more components in the composite input feed composition, such as $CO_2$ for instance, from highest concentration "first" to lowest concentration "last" with approximately similar compositional distinctions representing the same ordinal level.)

Yet another additional or alternate option can be to specify the anode fuel utilization corresponding to a particular cathode stage (again, where fuel cells/stacks can be arranged at least partially in one or more series arrangements). As noted above, based on the direction of the flows within the anodes and cathodes, the first cathode stage may not correspond to (be across the same fuel cell membrane from) the first anode stage. Thus, in some aspects of the invention, the anode fuel utilization can be specified for the first cathode stage in a series, the second cathode stage in a series, the final cathode stage in a series, or any other convenient cathode stage in a series.

Yet still another additional or alternate option can be to specify an overall average of fuel utilization over all fuel cells in a fuel cell array. In various aspects, the overall average of fuel utilization for a fuel cell array can be about 65% or less, for example, about 60% or less, about 55% or less, about 50% or less, or about 45% or less (additionally or alternately, the overall average fuel utilization for a fuel cell array can be at least about 25%, for example at least about 30%, at least about 35%, or at least about 40%). Such an average fuel utilization need not necessarily constrain the fuel utilization in any single stage, so long as the array of fuel cells meets the desired fuel utilization.

Applications for $CO_2$ Output after Capture

In various aspects of the invention, the systems and methods described above can allow for production of carbon dioxide as a pressurized fluid. For example, the $CO_2$ generated from a cryogenic separation stage can initially correspond to a pressurized $CO_2$ liquid with a purity of at least about 90%, e.g., at least about 95%, at least about 97%, at least about 98%, or at least about 99%. This pressurized $CO_2$ stream can be used, e.g., for injection into wells in order to further enhance oil or gas recovery such as in secondary oil recovery. When done in proximity to a facility that encompasses a gas turbine, the overall system may benefit from additional synergies in use of electrical/mechanical power and/or through heat integration with the overall system.

Alternatively, for systems dedicated to an enhanced oil recovery (EOR) application (i.e., not comingled in a pipeline system with tight compositional standards), the $CO_2$ separation requirements may be substantially relaxed. The EOR application can be sensitive to the presence of $O_2$, so $O_2$ can be absent, in some embodiments, from a $CO_2$ stream intended for use in EOR. However, the EOR application can tend to have a low sensitivity to dissolved CO, $H_2$, and/or $CH_4$. Also, pipelines that transport the $CO_2$ can be sensitive to these impurities. Those dissolved gases can typically have only subtle impacts on the solubilizing ability of $CO_2$ used for EOR. Injecting gases such as CO, $H_2$, and/or $CH_4$ as EOR gases can result in some loss of fuel value recovery, but such gases can be otherwise compatible with EOR applications.

Additionally or alternately, a potential use for $CO_2$ as a pressurized liquid can be as a nutrient in biological processes such as algae growth/harvesting. The use of MCFCs for $CO_2$ separation can ensure that most biologically significant pollutants could be reduced to acceptably low levels, resulting in a $CO_2$-containing stream having only minor amounts of other "contaminant" gases (such as CO, $H_2$, $N_2$, and the like, and combinations thereof) that are unlikely to substantially negatively affect the growth of photosynthetic organisms. This can be in stark contrast to the output streams generated by most industrial sources, which can often contain potentially highly toxic material such as heavy metals.

In this type of aspect of the invention, the $CO_2$ stream generated by separation of $CO_2$ in the anode loop can be used to produce biofuels and/or chemicals, as well as precursors thereof. Further additionally or alternately, $CO_2$ may be produced as a dense fluid, allowing for much easier pumping and transport across distances, e.g., to large fields of photosynthetic organisms. Conventional emission sources can emit hot gas containing modest amounts of $CO_2$ (e.g., about 4-15%) mixed with other gases and pollutants. These materials would normally need to be pumped as a dilute gas to an algae pond or biofuel "farm". By contrast, the MCFC system according to the invention can produce a concentrated $CO_2$ stream (~60-70% by volume on a dry basis) that can be concentrated further to 95%+ (for example 96%+, 97%+, 98%+, or 99%+) and easily liquefied. This stream can then be transported easily and efficiently over long distances at relatively low cost and effectively distributed over a wide area. In these embodiments, residual heat from the combustion source/MCFC may be integrated into the overall system as well.

An alternative embodiment may apply where the $CO_2$ source/MCFC and biological/chemical production sites are co-located. In that case, only minimal compression may be necessary (i.e., to provide enough $CO_2$ pressure to use in the biological production, e.g., from about 15 psig to about 150 psig). Several novel arrangements can be possible in such a case. Secondary reforming may optionally be applied to the anode exhaust to reduce $CH_4$ content, and water-gas shift may optionally additionally or alternately be present to drive any remaining CO into $CO_2$ and $H_2$.

The components from an anode output stream and/or cathode output stream can be used for a variety of purposes. One option can be to use the anode output as a source of hydrogen, as described above. For an MCFC integrated with or co-located with a refinery, the hydrogen can be used as a hydrogen source for various refinery processes, such as hydroprocessing. Another option can be to additionally or alternately use hydrogen as a fuel source where the $CO_2$ from combustion has already been "captured." Such hydrogen can be used in a refinery or other industrial setting as a fuel for a boiler, furnace, and/or fired heater, and/or the hydrogen can be used as a feed for an electric power generator, such as a turbine. Hydrogen from an MCFC fuel cell can further additionally or alternately be used as an input stream for other types of fuel cells that require hydrogen as an input, possibly including vehicles powered by fuel cells. Still another option can be to additionally or alternately use syngas generated as an output from an MCFC fuel cell as a fermentation input.

Another option can be to additionally or alternately use syngas generated from the anode output. Of course, syngas can be used as a fuel, although a syngas based fuel can still lead to some $CO_2$ production when burned as fuel. In other aspects, a syngas output stream can be used as an input for a chemical synthesis process. One option can be to additionally or alternately use syngas for a Fischer-Tropsch type process, and/or another process where larger hydrocarbon molecules are formed from the syngas input. Another option can be to additionally or alternately use syngas to form an intermediate product such as methanol. Methanol could be used as the final product, but in other aspects methanol generated from syngas can be used to generate larger compounds, such as gasoline, olefins, aromatics, and/or other products. It is noted that a small amount of $CO_2$ can be acceptable in the syngas feed to a methanol synthesis process, and/or to a Fischer-Tropsch process utilizing a shifting catalyst. Hydroformylation is an additional or alternate example of still another synthesis process that can make use of a syngas input.

It is noted that one variation on use of an MCFC to generate syngas can be to use MCFC fuel cells as part of a system for processing methane and/or natural gas withdrawn by an offshore oil platform or other production system that is a considerable distance from its ultimate market. Instead of attempting to transport the gas phase output from a well, or attempting to store the gas phase product for an extended period, the gas phase output from a well can be used as the input to an MCFC fuel cell array. This can lead to a variety of benefits. First, the electric power generated by the fuel cell array can be used as a power source for the platform. Additionally, the syngas output from the fuel cell array can be used as an input for a Fischer-Tropsch process at the production site. This can allow for formation of liquid hydrocarbon products more easily transported by pipeline, ship, or railcar from the production site to, for example, an on-shore facility or a larger terminal.

Still other integration options can additionally or alternately include using the cathode output as a source of higher purity, heated nitrogen. The cathode input can often include a large portion of air, which means a substantial portion of nitrogen can be included in the cathode input. The fuel cell can transport $CO_2$ and $O_2$ from the cathode across the electrolyte to the anode, and the cathode outlet can have lower concentrations of $CO_2$ and $O_2$, and thus a higher concentration of $N_2$ than found in air. With subsequent removal of the residual $O_2$ and $CO_2$, this nitrogen output can be used as an input for production of ammonia or other nitrogen-containing chemicals, such as urea, ammonium nitrate, and/or nitric acid. It is noted that urea synthesis could additionally or alternately use $CO_2$ separate from the anode output as an input feed.

Example of Configuration for Integration of MCFC with Blast Furnace

This example demonstrates an integrated MCFC system with an iron blast furnace, which reduced $Fe_2O_3$ to pig iron (95% Fe). The reaction system configuration for this example was similar to the configuration shown in FIG. 4. In this example, the MCFC system was operated at 30% fuel utilization with a methane-steam feed to the anode to produce reducing gas for the blast furnace. The blast furnace off gas was heat integrated with the MCFC inlet/outlet and a fraction of it can be used as the cathode feed, while the remainder can be emitted to the atmosphere or compressed for $CO_2$ sequestration in a low $CO_2$ emissions iron/steel production scheme.

The integrated MCFC process was sized to produce enough reducing gas to operate the blast furnace of a ~2.8 Mton/year steel plant. In addition to generating the reducing gas feed for the blast furnace based on the anode exhaust, the MCFC also produced about 233 MW of power which could be used to power other parts of the steel plant, to power separation and compression of $CO_2$ for pipeline transport (such as $CO_2$ stream 411 as shown in FIG. 4), and/or to be sold back to the grid. FIG. 5 shows representative values for the flow composition at various locations in a system having a configuration similar to the configuration shown in FIG. 4. For convenience, the stream designations shown in FIG. 4 were also used to designate the streams in FIG. 5. It is noted that the composition of anode output stream 403 was based on a fuel utilization in the anode of about 30%. The changes in the relative composition of streams 404 and 405 were due to equilibration via the water gas shift reaction. It is noted that the composition of blast furnace off gas 406 was based on simulated consumption of ~100% of the reducing gas in the blast furnace, while no methane was consumed in the furnace. In a real system, it is likely that an excess of reducing gas would be used to provide process stability. Additionally, it is likely that a small amount of methane would be consumed in the blast furnace via reaction with previously reduced iron, potentially leading to introduction of minor additional carbon into the iron as well as production of additional $H_2$. However, this idealized calculation of the composition of blast furnace off gas 406 provides representative values for the energy content and composition.

It is noted that a conventional configuration for a similarly sized steel plant was reported in a journal article by Arasto et al. (Title: Post-combustion capture of $CO_2$ at an integrated steel mill—Part I: Technical concept analysis; Antti Arastoa, Eemeli Tsuparia, Janne Kärkia, Erkki Pisilä, Lotta Sorsamakia, International Journal of Greenhouse Gas Control, 16, (2013) p. 271-277). The configuration in Arasto et al. produced 135 MW with an HRSG-turbine system that recovered heat from the traditional coal burners and blast furnace. This was enough power to operate the ~2.8 Mton/year steel plant, provide electricity to a local community, and export some to the gird. By contrast, by using an MCFC for power generation on the methane feed, as opposed to generating power from the excess heat of the steel plant, the MCFC in this example generated about 233 MW of power. Compared to the conventional steel plant configuration reported in Arasto et al., the integrated MCFC-blast furnace system can produce more power, and can also reduce the $CO_2$ emissions by at least 65%.

Additional Embodiments

Embodiment 1. A method for producing iron and/or steel, the method comprising: introducing a fuel stream comprising a reformable fuel into an anode of a molten carbonate fuel cell, an internal reforming element associated with the anode, or a combination thereof; introducing a cathode inlet stream comprising $CO_2$ and $O_2$ into a cathode of the molten carbonate fuel cell; generating electricity within the molten carbonate fuel cell; withdrawing, from an anode exhaust, a first gas stream comprising CO, the anode exhaust having a pressure of about 500 kPag or less; and introducing the first gas stream withdrawn from the anode exhaust into a process for production of iron and/or steel.

Embodiment 2. The method of Embodiment 1, further comprising using the electricity generated to provide heat to the process for production of iron and/or steel.

Embodiment 3. The method of any of the above embodiments, further comprising withdrawing a second gas stream comprising $H_2$ from the anode exhaust, and using the second gas stream as fuel for heating the process for production of iron and/or steel.

Embodiment 4. The method of any of the above embodiments, further comprising separating water from the anode exhaust, the first gas stream withdrawn from the anode exhaust, or a combination thereof, and washing a process slag using the separated water.

Embodiment 5. The method of any of the above embodiments, wherein the cathode inlet stream comprises at least a portion of a $CO_2$-containing exhaust produced by the process for production of iron and/or steel.

Embodiment 6. The method of Embodiment 5, further comprising separating $CO_2$ from the $CO_2$-containing exhaust produced by the process for production of iron and/or steel.

Embodiment 7. The method of any of the above embodiments, further comprising exposing the first withdrawn gas stream to a water gas shift catalyst under effective water gas shift conditions prior to introducing the withdrawn first gas stream into the process for production of iron and/or steel.

Embodiment 8. The method of any of the above embodiments, wherein the molten carbonate fuel cell is operated to generate electricity at a thermal ratio of about 1.0 or less, the method further comprising transferring heat from the process for production of iron and/or steel (e.g., from a furnace) to the molten carbonate fuel cell, wherein a temperature of the anode exhaust is greater than a temperature at an anode inlet.

Embodiment 9. The method of Embodiment 8, wherein transferring heat comprises performing heat exchange between the anode inlet stream and at least one of an iron and/or steel production process furnace and an iron and/or steel production process exhaust, wherein performing the heat exchange optionally comprises increasing a temperature of the anode inlet stream by at least about 100° C. (e.g., by at least about 150° C.

Embodiment 10. The method of any of the above Embodiments, further comprising exposing the withdrawn gas stream to a water gas shift catalyst under effective water gas shift conditions prior to introducing the gas stream into the process for production of iron and/or steel.

Embodiment 11. The method of any of the above embodiments, further comprising separating water from the anode exhaust, the withdrawn first gas stream, or a combination thereof, and washing a process slag using the separated water.

Embodiment 12. The method of any of the previous embodiments, wherein an amount of the reformable fuel introduced into the anode, into the internal reforming element associated with the anode, or into the combination thereof, provides a reformable fuel surplus ratio of at least about 1.5 (e.g., at least about 2.0, at least about 2.5, or at least about 3.0).

Embodiment 13. The method of any of the above Embodiments, the method further comprising reforming the reformable fuel, wherein at least about 90% of the reformable fuel introduced into the anode, the reforming stage associated with the anode, or a combination thereof is reformed in a single pass through the anode.

Embodiment 14. The method of any of the above embodiments, wherein a ratio of net moles of syngas in a fuel cell anode exhaust to moles of $CO_2$ in a fuel cell cathode exhaust is at least about 2.0 (e.g., at least about 3.0, at least about 4.0, at least about 5.0, at least about 10.0, or at least about 20.0), and optionally about 40.0 or less (e.g., about 30.0 or less or about 20.0 or less).

Embodiment 15. The method of any of the above Embodiments, wherein a fuel utilization in the anode is about 65% or less (e.g., about 60% or less, about 50% or less, about 40% or less, about 30% or less, about 25% or less, or about 20% or less) and a $CO_2$ utilization in the cathode is at least about 50% (e.g., at least about 60%, at least about 65%, at least about 70%, or at least about 75%).

Embodiment 16. The method of any of the above Embodiments, wherein an electrical efficiency for the molten carbonate fuel cell is between about 10% and about 40% (e.g., between about 10% and about 35%, between about 10% and about 30%, between about 10% and about 25%, between about 10% and about 20%) and a total fuel cell efficiency for the fuel cell of at least about 50% (e.g., at least about 55%, at least about 60%, at least about 65%, at least about 70%, at least about 75%, or at least about 80%).

Embodiment 17. The method of any of the above embodiments, wherein the anode exhaust has a molar ratio of $H_2$:CO of at least about 3.0:1 (e.g., at least about 4.0:1, from about 3.0:1 to about 10:1, or from about 4.0:1 to about 10:1).

Embodiment 18. The method of any of the above embodiments, wherein at least about 90 vol % of the reformable fuel is methane.

Embodiment 19. The method of any of the above Embodiments, wherein less than 10 vol % of $H_2$ produced in the anode in a single pass is directly or indirectly recycled to the anode or to the cathode.

Embodiment 20. The method of any of the above Embodiments, wherein a reformable hydrogen content of the reformable fuel introduced into the anode, a reforming stage associated with the anode, or a combination thereof is at least about 50% greater (e.g., at least about 75% greater or at least about 100% greater) than an amount of hydrogen reacted to generate electricity.

Embodiment 21. The method of any of the above embodiments, wherein the molten carbonate fuel cell further comprises one or more integrated endothermic reaction stages.

Embodiment 22. The method of Embodiment 21, wherein at least one of the integrated endothermic reaction stages comprises an integrated reforming stage, the fuel stream introduced into the anode optionally being passed through at least one of the integrated reforming stages prior to entering the anode.

Embodiment 23. The method of any of the above Embodiments, wherein the molten carbonate fuel cell is operated at a first operating condition to generate electrical power and at least about 30 mW/cm$^2$ (e.g., at least about 40 mW/cm$^2$, at least about 50 mW/cm$^2$, or at least 100 mW/cm$^2$) of waste heat, the first operating condition providing a current density of at least about 150 mA/cm$^2$, and wherein an effective amount of an endothermic reaction is performed to maintain a temperature differential between an anode inlet and an anode outlet of about 100° C. or less (e.g., about 80° C. or less or about 60° C. or less).

Embodiment 24. The method of embodiment 23, wherein performing the endothermic reaction consumes at least about 40% (e.g., at least about 50%, at least about 60%, or at least about 75%) of the waste heat.

Embodiment 25. The method of any of the above embodiments, wherein the molten carbonate fuel cell is operated at a voltage $V_A$ of less than about 0.68V (e.g., less than about 0.67V, less than about 0.66V, or about 0.65V or less), and optionally of at least about 0.60V (e.g., at least about 0.61V, at least about 0.62V, or at least about 0.63V).

Embodiment 26. The method of any of the above Embodiments, further comprising reforming the reformable fuel, wherein at least about 90% of the reformable fuel introduced into the anode, the reforming stage associated with the anode, or a combination thereof is reformed in a single pass through the anode.

Although the present invention has been described in terms of specific embodiments, it is not necessarily so limited. Suitable alterations/modifications for operation under specific conditions should be apparent to those skilled in the art. It is therefore intended that the following claims be interpreted as covering all such alterations/modifications that fall within the true spirit/scope of the invention.

What is claimed is:

1. A method for producing iron and/or steel, the method comprising:
   introducing a fuel stream comprising a reformable fuel into an anode of a molten carbonate fuel cell, an internal reforming element associated with the anode, or a combination thereof, thereby forming an anode exhaust comprising one or more anode exhaust components;
   introducing a cathode inlet stream comprising $CO_2$ and $O_2$ into a cathode of the molten carbonate fuel cell, thereby forming a cathode exhaust comprising one or more cathode exhaust components;
   generating electricity within the molten carbonate fuel cell; and
   conducting a process for producing iron and/or steel, which consumes, as an input thereto, an output from the molten carbonate fuel cells, and/or which provides, as an output therefrom, an input into an element of the molten carbonate fuel cell.

2. The method of claim 1, wherein the electricity generated by the molten carbonate fuel cell is used to provide heat to the process for production of iron and/or steel.

3. The method of claim 1, wherein a gas stream comprising $H_2$ is withdrawn from the anode exhaust and used as fuel for heating the process for producing iron and/or steel.

4. The method of claim 1, wherein water is separated from the anode exhaust, the gas stream withdrawn from the anode exhaust, or a combination thereof, and a process slag in the process for producing iron and/or steel is washed using the separated water.

5. The method of claim 1, wherein the cathode inlet stream comprises at least a portion of a $CO_2$-containing exhaust generated by the process for producing iron and/or steel.

6. The method of claim 5, further comprising separating $CO_2$ from the $CO_2$-containing exhaust generated by the process for producing iron and/or steel.

7. The method of claim 1, wherein the molten carbonate fuel cell is operated to generate electricity at a thermal ratio of about 1.3 or less at steady state operation, the method further comprising transferring heat from the process for producing iron and/or steel to the molten carbonate fuel cell.

8. The method of claim 7, wherein a temperature of the anode exhaust is greater than a temperature at an anode inlet.

9. The method of claim 7, wherein transferring heat from the process for producing iron and/or steel comprises performing heat exchange between an anode inlet stream and at least one of an iron and/or steel production process furnace and an iron and/or steel production process exhaust.

10. The method of claim 9, wherein performing the heat exchange comprises increasing a temperature of the anode inlet stream by at least about 100° C.

11. The method of claim 1, wherein the molten carbonate fuel cell is operated at a thermal ratio from about 0.25 to about 1.15.

12. The method of claim 1, further comprising separating at least one of $CO_2$ and $H_2O$ from the anode exhaust in one or more separation stages.

13. The method of claim 1, wherein an amount of the reformable fuel introduced into the anode, the internal reforming element associated with the anode, or the combination thereof, provides a reformable fuel surplus ratio of at least about 1.5.

14. The method of claim 1, wherein a ratio of net moles of syngas in the anode exhaust to moles of $CO_2$ in a cathode exhaust is at least about 2.0.

15. The method of claim 1, wherein a fuel utilization in the anode is about 50% or less and a $CO_2$ utilization in the cathode is at least about 60%.

16. The method of claim 1, wherein the molten carbonate fuel cell is operated to generate electrical power at a current density of at least about 150 $mA/cm^2$ and at least about 40 $mW/cm^2$ of waste heat, the method further comprising performing an effective amount of an endothermic reaction to maintain a temperature differential between an anode inlet and an anode outlet of about 100° C. or less.

17. The method of claim 16, wherein performing the endothermic reaction consumes at least about 40% of the waste heat.

18. The method of claim 1, wherein an electrical efficiency for the molten carbonate fuel cell is between about 10% and about 40% and a total fuel cell efficiency for the molten carbonate fuel cell is at least about 55%.

19. The method of claim 1, wherein at least about 90 vol % of the reformable fuel is methane.

* * * * *